United States Patent
Yoshino et al.

(10) Patent No.: US 11,161,867 B2
(45) Date of Patent: Nov. 2, 2021

(54) COMPOUND, RAW MATERIAL FOR FORMING THIN FILM, METHOD FOR MANUFACTURING THIN FILM, AND AMIDINE COMPOUND

(71) Applicant: ADEKA CORPORATION, Tokyo (JP)

(72) Inventors: Tomoharu Yoshino, Tokyo (JP); Nana Okada, Tokyo (JP); Akihiro Nishida, Tokyo (JP); Atsushi Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 159 days.

(21) Appl. No.: 16/346,724

(22) PCT Filed: Oct. 5, 2017

(86) PCT No.: PCT/JP2017/036318
§ 371 (c)(1),
(2) Date: May 1, 2019

(87) PCT Pub. No.: WO2018/088079
PCT Pub. Date: May 17, 2018

(65) Prior Publication Data
US 2020/0055887 A1 Feb. 20, 2020

(30) Foreign Application Priority Data
Nov. 8, 2016 (JP) .............................. JP2016-217749

(51) Int. Cl.
*C07F 15/06* (2006.01)
*C07C 251/08* (2006.01)
*C23C 16/06* (2006.01)
*C23C 16/455* (2006.01)

(52) U.S. Cl.
CPC .......... *C07F 15/065* (2013.01); *C07C 251/08* (2013.01); *C23C 16/06* (2013.01); *C23C 16/45553* (2013.01)

(58) Field of Classification Search
CPC .................................................. C07C 257/14
USPC ....................................................... 106/1.012
See application file for complete search history.

(56) References Cited

FOREIGN PATENT DOCUMENTS

| | | |
|---|---|---|
| GB | 1 209 997 | 10/1970 |
| JP | 2004-2306 | 1/2004 |
| JP | 2006-511716 | 4/2006 |
| JP | 2008/502680 | 1/2008 |
| JP | 2009-504913 | 2/2009 |
| JP | 2013-104100 | 5/2013 |
| JP | 2013-545755 | 12/2013 |
| JP | 2014-511380 | 5/2014 |
| WO | 2009/094262 | 7/2009 |
| WO | 2009/094263 | 7/2009 |
| WO | WO 2009/094263 A1 * 7/2009 ............. C07F 15/00 |
| WO | 2009/105668 | 8/2009 |

OTHER PUBLICATIONS

International Search Report dated Jan. 9, 2018 in International (PCT) Application No. PCT/JP2017/036318.

\* cited by examiner

*Primary Examiner* — Ana Z Muresan
(74) *Attorney, Agent, or Firm* — Wenderoth, Lind & Ponack, L.L.P.

(57) ABSTRACT

A raw material for forming a thin film, comprising a compound represented by General Formula (1) below.

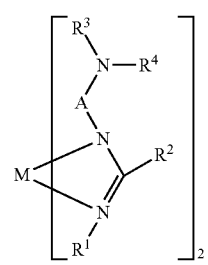

(in the formula, $R^1$ represents a linear or branched alkyl group having 1 to 5 carbon atoms, $R^2$ represents hydrogen or a linear or branched alkyl group having 1 to 5 carbon atoms, $R^3$ and $R^4$ each independently represent a linear or branched alkyl group having 1 to 5 carbon atoms, A represents an alkanediyl group having 1 to 4 carbon atoms and M represents copper, iron, nickel, cobalt or manganese.).

4 Claims, 4 Drawing Sheets

COMPOUND, RAW MATERIAL FOR FORMING THIN FILM, METHOD FOR MANUFACTURING THIN FILM, AND AMIDINE COMPOUND

TECHNICAL FIELD

The present invention relates to a novel compound, a raw material for forming a thin film that includes the compound, a method for manufacturing a thin film by using the raw material for forming a thin film, and a novel amidine compound.

BACKGROUND ART

Thin-film materials including a metal element have been used for a variety of applications because such materials exhibit electric properties, optical properties and the like. For example, copper and copper-containing thin films have been used as wiring materials for LSI because of a high electric conductivity, high resistance to electromigration, and a high melting point. Further, nickel and nickel-containing thin films are mainly used for parts of electronic components such as resistive films and barrier films, parts for recording media such as magnetic films, and parts for thin-film solar cells, such as electrodes. Cobalt and cobalt-containing thin films have been used for electrode films, resistive films, adhesive films, magnetic tapes, ultra-hard tool members and the like.

Examples of methods for manufacturing such thin films include a sputtering method, an ion plating method, a MOD method such as a coating pyrolysis method and a sol-gel method, and a chemical vapor deposition method. Among them, the chemical vapor deposition (referred to hereinbelow simply as CVD) method, inclusive of an atomic layer deposition (referred to hereinbelow simply as ALD) method, is an optimum manufacturing process because it has advantages such as being suitable for mass production, excelling in composition controllability and stepwise coating ability, and enabling hybrid accumulation.

A large number of various materials have been reported as metal-supplying sources for use in the chemical vapor deposition method. For example, Patent Document 1 discloses a method of forming a metal-containing thin film by using a volatile metal amidinate. Further, Patent Document 2 discloses a diazadiene-based metal compound that can be used in a chemical vapor deposition or atomic layer deposition. Patent Documents 1 and 2 do not describe a compound of the present invention.

Patent Document 1: Japanese Patent Application Laid-open No. 2006-511716
Patent Document 2: Japanese Patent Application Laid-open No. 2013-545755

SUMMARY OF INVENTION

Technical Problem

When a metal-containing thin film is formed on a surface of a substrate by vaporizing a raw material for chemical vapor deposition, raw materials for forming a thin film, which have a high vapor pressure and a low melting point and are capable of manufacturing a high-quality metal-containing thin film, are required. Conventional raw materials for forming a thin film have not exhibited these characteristics. In particular, materials with a low melting point have been strongly required, since there is a need to increase the transportability of a raw material for forming a thin film in order to improve the productivity.

Solution to the Problem

The present inventors have carried out investigations and discovered that the abovementioned problems can be solved by a specific compound, to achieve the present invention.

The present invention provides a compound represented by General Formula (1) below, a raw material for forming a thin film that includes the compound, and a method for manufacturing a thin film by using the raw material.

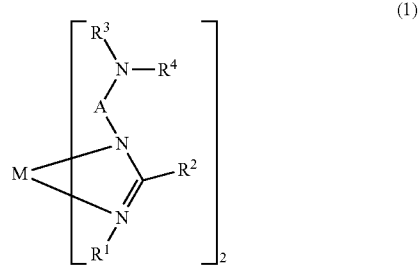

(1)

In the formula, $R^1$ represents a linear or branched alkyl group having 1 to 5 carbon atoms, $R^2$ represents hydrogen or a linear or branched alkyl group having 1 to 5 carbon atoms, $R^3$ and $R^4$ each independently represent a linear or branched alkyl group having 1 to 5 carbon atoms, A represents an alkanediyl group having 1 to 4 carbon atoms and M represents copper, iron, nickel, cobalt or manganese.

The present invention also provides an amidine compound represented by General Formula (2) below.

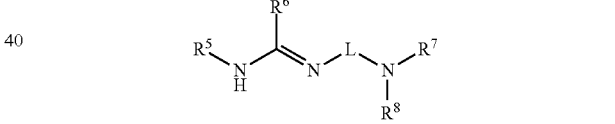

(2)

In the formula, $R^5$ represents a linear or branched alkyl group having 1 to 5 carbon atoms, $R^6$ represents hydrogen or a linear or branched alkyl group having 1 to 5 carbon atoms, $R^7$ and $R^8$ each independently represent a linear or branched alkyl group having 1 to 5 carbon atoms, L represents an alkanediyl group having 1 to 4 carbon atoms. Provided that when $R^5$ represents ethyl group and $R^6$ represents hydrogen, L represents a branched alkanediyl group having 3 carbon atoms or an alkanediyl group having 4 carbon atoms. Provided that when $R^5$ represents ethyl group or tert-butyl group and $R^6$ represents methyl group, L represents an alkanediyl group having 3 or 4 carbon atoms.

Advantageous Effects of the Invention

In accordance with the present invention, it is possible to obtain a compound having a high vapor pressure and a low melting point, which becomes a liquid at normal pressure and 30° C. or becomes a liquid by slight heating. The compound is particularly suitable as a raw material for forming a metal-containing thin film by a CVD method, in particular, can be preferably used as a raw material for forming a metal-containing thin film by an ALD method.

Further, when the cobalt-containing compound of the present invention is used as a raw material for forming a thin film by the ALD method, a cobalt-containing thin film can be selectively formed only on a pattern of a copper layer or ruthenium layer which is previously formed on a silicon substrate or silicon oxide substrate, because there is a unique property that a cobalt-containing thin film cannot be formed on the surface of the silicon substrate and silicon oxide substrate.

In accordance with the present invention, it is possible to obtain an amidine compound that can be used for synthesizing the compound described above.

DESCRIPTION OF EMBODIMENTS

Figure 1:
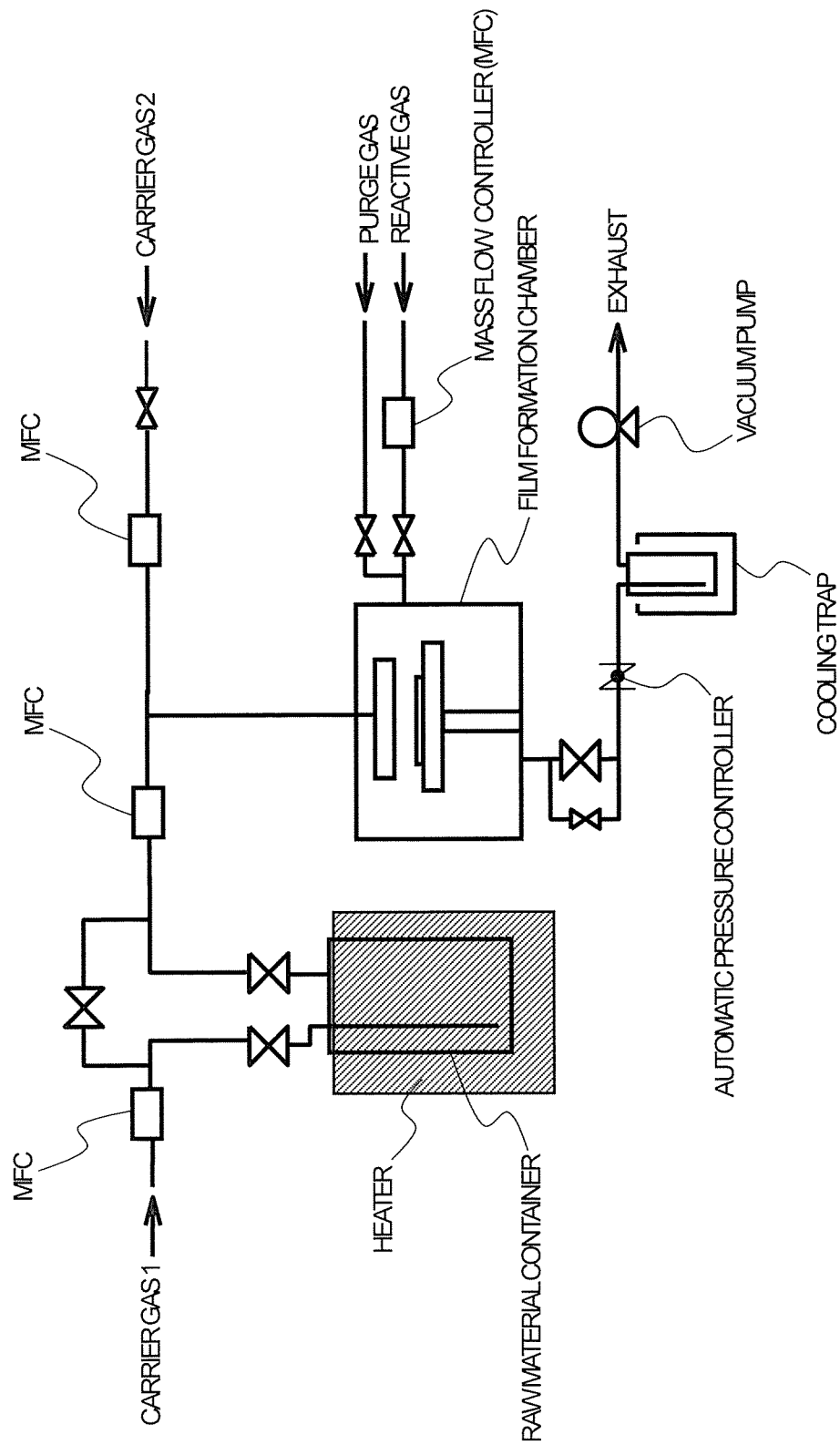
FIG. 1 is a conceptual diagram illustrating an example of a chemical vapor deposition apparatus for use in the method for manufacturing a thin film in the present invention.

The compound in accordance with the present invention is represent by General Formula (1) above. This compound is suitable as a precursor for a thin film manufacturing method having a vaporization step, such as the CVD method, and can be used for forming a thin film using the ALD method. The compound in accordance with the present invention is a compound with a low melting point, which becomes a liquid at normal pressure and 30° C. or becomes a liquid by slight heating. Since the compound having a low melting point has good transportability, the compound of the present invention is suitable as a precursor for a thin film production method having a vaporization step, such as the CVD method.

Examples of the linear or branched alkyl group having 1 to 5 carbon atoms, which is represented by $R^1$, $R^2$, $R^3$ and $R^4$ in General Formula (1) above, include methyl group, ethyl group, propyl group, isopropyl group, butyl group, isobutyl group, sec-butyl group, tert-butyl group, pentyl group, isopentyl group, and the like.

Examples of the alkanediyl group having 1 to 4 carbon atoms, which is represented by A in General Formula (1) above, include methylene group, ethylene group, propane-1,3-diyl group, propane-1,2-diyl group, butylene group, butane-1,3-diyl group, butane-2,3-diyl group, butane-1,2-diyl group, and the like.

M in General Formula (1) above represents copper, iron, nickel, cobalt or manganese. Among them, the compound where M is copper, cobalt or nickel is preferred, because the compound has a low melting point and can form a thin film having a low residual carbon content by the ALD method. In particular, the compound where M is cobalt is preferred, because the compound can form a high-quality cobalt atom-containing thin film.

The compound where $R^1$ in General Formula (1) above is a sec- or tert-alkyl group having 3 to 5 carbon atoms is preferred, because the compound has a low melting point. The compound where $R^1$ is a tert-alkyl group having 3 to 5 carbon atoms is particularly preferred. The compound where $R^2$ in General Formula (1) above is hydrogen, methyl group or ethyl group is preferred, because the compound has a low melting point and a high vapor pressure. In particular, the compound where $R^2$ is methyl group is particularly preferred. The compound where $R^3$ and $R^4$ in General Formula (1) above are methyl group or ethyl group is preferred, because the compound has a low melting point and a high vapor pressure. In particular, the compound where $R^3$ and $R^4$ are methyl group is particularly preferred. The compound where A in General Formula (1) above is ethylene group, propane-1,3-diyl group or propane-1,2-diyl group is preferred, because the compound has a low melting point and a high vapor pressure. In particular, the compound where A is propane-1,2-diyl group is particularly preferred. In methods for producing thin films by MOD methods without a vaporization step, R to $R^4$ and A may be appropriately selected depending on the solubility in a solvent used, the thin film forming reaction and the like.

Preferred specific examples of the compound where M in General Formula (1) above is cobalt include Compounds No. 1 to No. 18 below. In Compounds No. 1 to No. 18 below, "Me" represents methyl group, "Et" represents ethyl group, and "tBu" represents tert-butyl group.

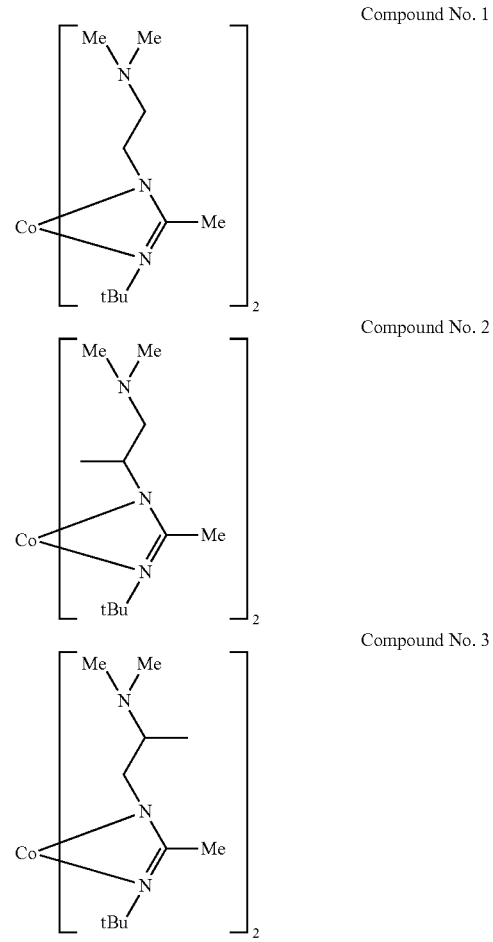

Compound No. 1

Compound No. 2

Compound No. 3

Compound No. 4
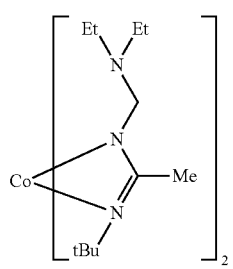
Compound No. 5
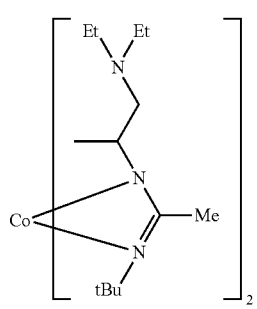
Compound No. 6
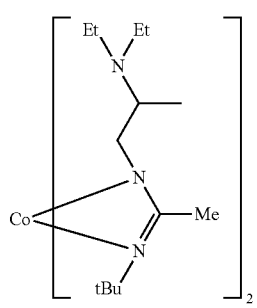
Compound No. 7
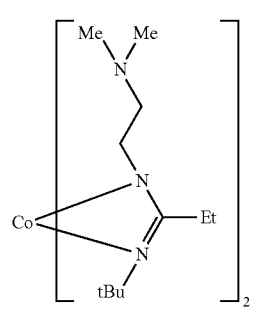
Compound No. 8
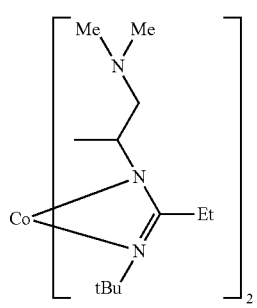
Compound No. 9
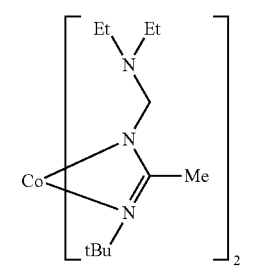
Compound No. 10
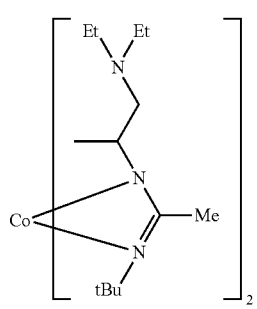
Compound No. 11
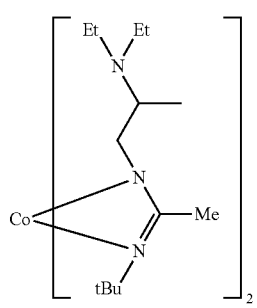
Compound No. 12
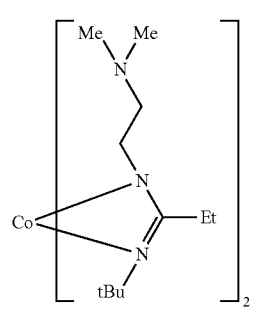
Compound No. 13
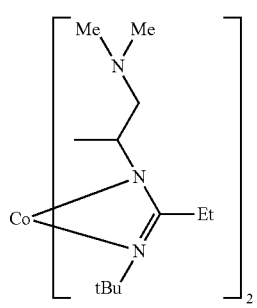

Compound No. 14
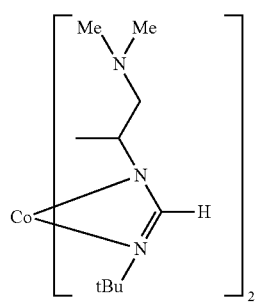

Compound No. 15
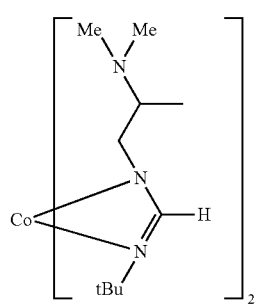

Compound No. 16
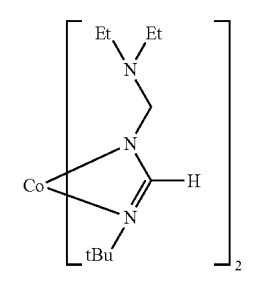

Compound No. 17
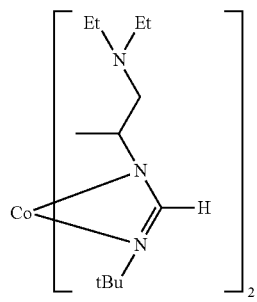

Compound No. 18
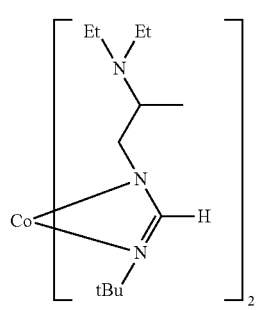

Preferred specific examples of the compound where M in General Formula (1) above is copper include Compounds No. 19 to No. 36 below. In Compounds No. 19 to No. 36 below, "Me" represents methyl group, "Et" represents ethyl group, and "tBu" represents tert-butyl group.

Compound No. 19
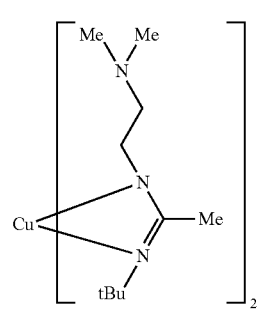

Compound No. 20
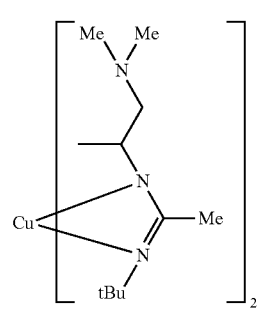

Compound No. 21
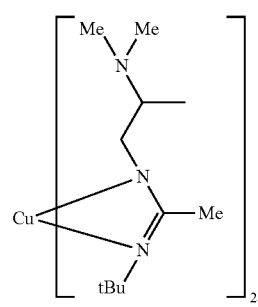

Compound No. 22
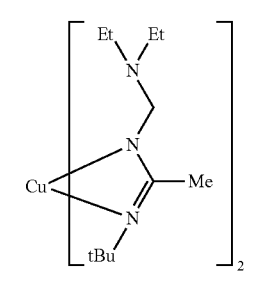

Compound No. 23
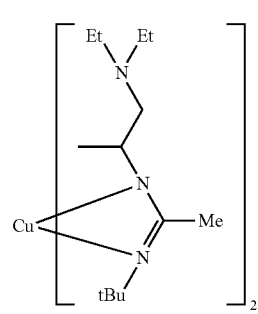

Compound No. 24
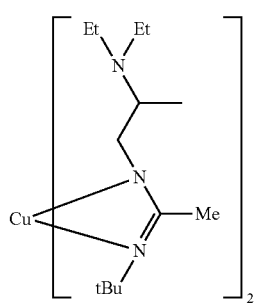
Compound No. 25
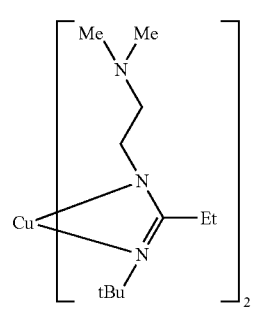
Compound No. 26
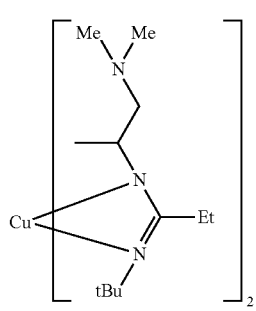
Compound No. 27
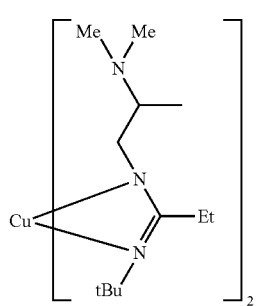
Compound No. 28
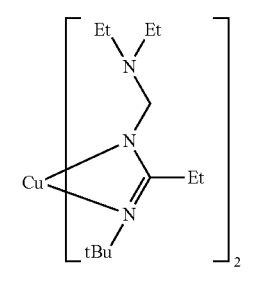
Compound No. 29
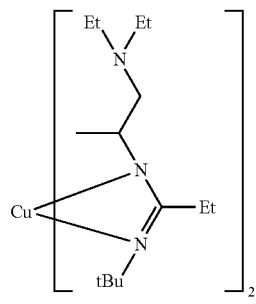
Compound No. 30
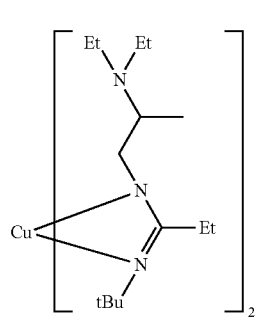
Compound No. 31
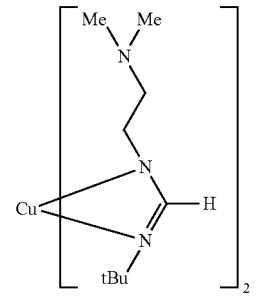
Compound No. 32
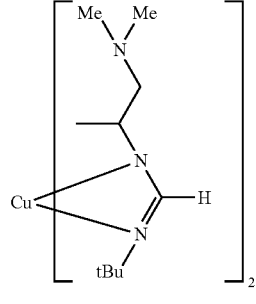
Compound No. 33
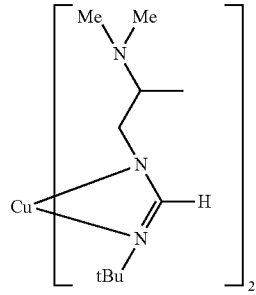

-continued

Compound No. 34
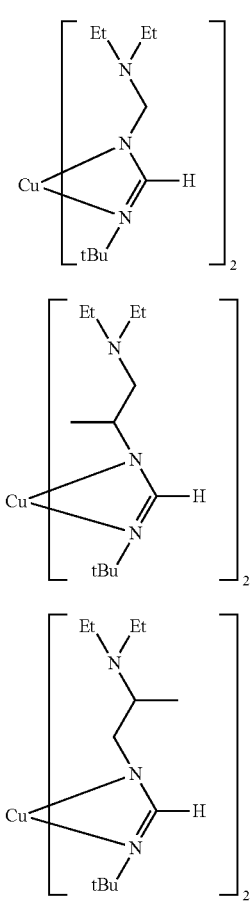

Compound No. 35

Compound No. 36
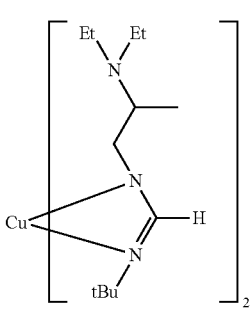

Preferred specific examples of the compound where M in General Formula (1) above is nickel include Compounds No. 37 to No. 54 below. In Compounds No. 37 to No. 54 below, "Me" represents methyl group, "Et" represents ethyl group, and "tBu" represents tert-butyl group.

Compound No. 37

Compound No. 38
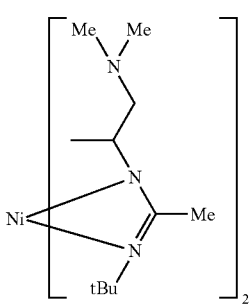

-continued

Compound No. 39
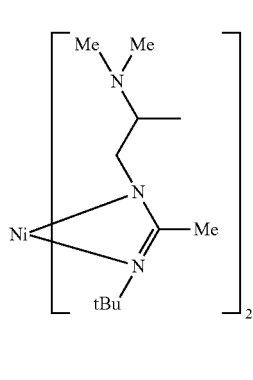

Compound No. 40

Compound No. 41
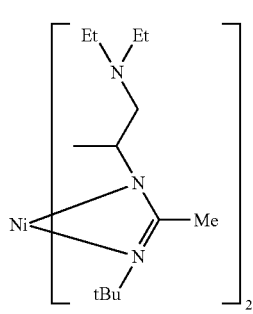

Compound No. 42
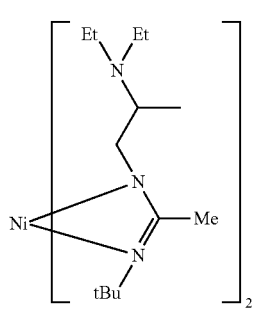

Compound No. 43
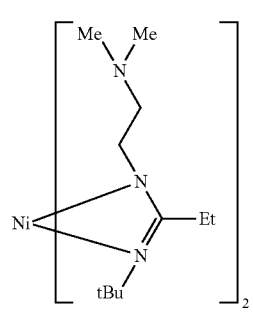

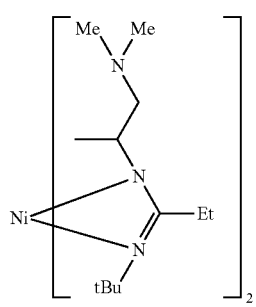
Compound No. 44
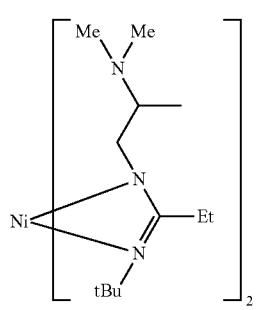
Compound No. 45
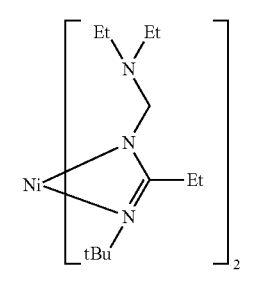
Compound No. 46
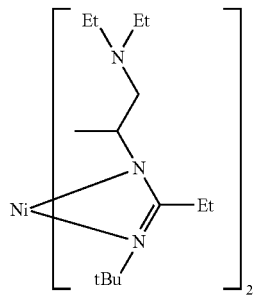
Compound No. 47
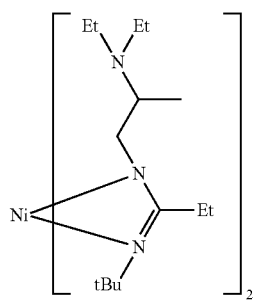
Compound No. 48
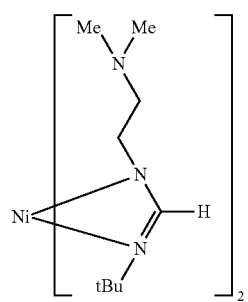
Compound No. 49
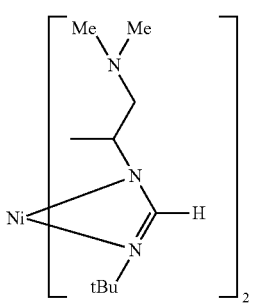
Compound No. 50
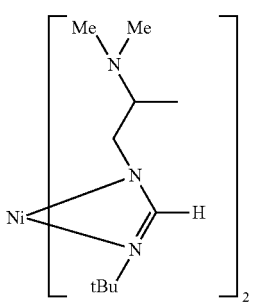
Compound No. 51
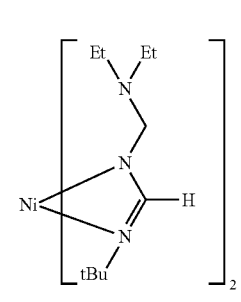
Compound No. 52
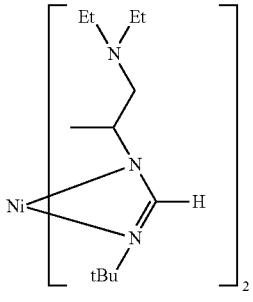
Compound No. 53

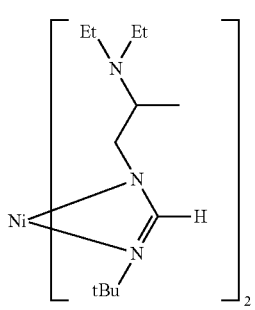

Compound No. 54

The compound of the present invention is not particularly restricted by the manufacturing method thereof and can be manufactured by using a well-known reaction.

Among the compounds represent by General Formula (1) above, a compound where M is cobalt can be manufactured, for example, by reacting cobalt(II) chloride with the corresponding amidine compound in the presence of n-butyllithium. A compound where M is copper, iron, nickel or manganese can be manufactured by the same method as the above manufacturing method except that a chloride of each metal is used as a starting material.

The raw material for forming a thin film of the present invention includes the compound of the present invention, which has been explained hereinabove, as a precursor for the thin film, and the form of the raw material differs depending on the manufacturing process in which the raw material for forming a thin film is to be used. For example, when a thin film including only one type of atom selected from a copper atom, iron atom, nickel atom, cobalt atom and manganese atom is manufactured, the raw material for forming a thin film of the present invention does not include metal compounds other than the abovementioned compound. On the other hand, when a thin film including metals and/or semimetals of two or more types is manufactured, the raw material for forming a thin film of the present invention includes, in addition to the abovementioned compound, a compound including the desired metal and/or a compound including the desired semimetal (can be also referred to hereinbelow as "other precursor"). As will be described hereinbelow, the raw material for forming a thin film of the present invention may additionally include an organic solvent and/or a nucleophilic reagent. Since physical properties of the compound serving as the precursor are advantageous for the CVD method and ALD method, the raw material for forming a thin film of the present invention is particularly useful as a raw material for chemical vapor deposition (referred to hereinbelow as "CVD").

Where the raw material for forming a thin film of the present invention is a raw material for chemical vapor deposition, the form thereof can be selected, as appropriate, according, e.g., to the delivery and feed method in the CVD method which is to be used.

The delivery and feed method can be a gas delivery method in which a CVD source is vaporized by heating and/or depressurizing the interior of a container in which the source is stored (can be referred to hereinbelow simply as "raw material container"), and the obtained vapor is introduced, optionally together with a carrier gas such as argon, nitrogen, and helium, into a film formation chamber in which a substrate is disposed (can be also referred to hereinbelow as "deposition reaction unit") or a liquid delivery method in which a CVD source is transported in a state of a liquid or solution into a vaporization chamber and vaporized by heating and/or depressurizing in the vaporization chamber, and the vapor is introduced into a film formation chamber. When the gas delivery method is used, the compound itself, which is represented by General Formula (1), can be used as the CVD source. When the liquid delivery method is used, the compound itself, which is represented by General Formula (1), or a solution obtained by dissolving the compound in an organic solvent can be used as the CVD source. Those CVD sources may additionally include the other precursor, a nucleophilic reagent or the like.

Further, CVD of a multicomponent system can be implemented by a method of vaporizing and feeding CVD sources for each component independently (can be also referred to hereinbelow as "single source method") and a method of vaporizing and feeding a mixed raw material obtained by mixing in advance multicomponent raw materials at the desired composition ratio (can be also referred to hereinbelow as "cocktail source method"). When the cocktail source method is used, a mixture of the compound of the present invention and the other precursor, or a mixed solution obtained by dissolving the mixture in an organic solvent can be used as the CVD source. The mixture or mixed solvent may additionally include a nucleophilic reagent.

The organic solvent is not particularly limited, and well-known typical organic solvents can be used. Examples of the organic solvents include acetates such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons including a cyano group such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. Such organic solvents may be used individually or as mixed solvents of two or more thereof according to the relationship between the solute solubility, usage temperature, boiling point, and flash point. When such organic solvents are used, the amount of the entire precursor in the CVD source which is a solvent in which the precursor is dissolved in the organic solvent is preferably 0.01 mol/L to 2.0 mol/L, in particular, 0.05 mol/L to 1.0 mol/L. The amount of the entire precursor, as referred to herein, is the amount of the compound of the present invention when the raw material for forming a thin film of the present invention does not include a metal compound and a semimetal compound other than the compound of the present invention, and is the total amount of the compound of the present invention and the other precursor when the raw material for forming a thin film of the present invention includes a compound (other precursor) including other metal and/or a compound including a semimetal in addition to the compound.

When CVD of a multicomponent system is performed, the other precursor which is used together with the compound of the present invention is not particularly limited, and any well-known typical precursor which has been used in CVD sources can be used.

Examples of the other precursor include one, or two or more compounds of silicon or a metal selected from a group including compounds having a hydride, a hydroxide, a halide, an azide, an alkyl, an alkenyl, a cycloalkyl, an aryl, an alkynyl, an amino, a dialkylaminoalkyl, a monoalkylamino, a dialkylamino, a diamine, a di(silyl-alkyl)amino, a di(alkyl-silyl)amino, a disilylamino, an alkoxy, an alkoxyalkyl, a hydrazido, a phosphido, a nitrile, a dialkylaminoalkoxy, an alkoxyalkyldialkylamino, a siloxy, a diketonate, a cyclopentadienyl, a silyl, a pyrazolate, a guanidinate, a phosphoguanidinate, an amidinate, a ketoiminate, a diketoiminate, a carbonyl, and a phosphoamidinate as a ligand.

Examples of metals for the precursor include magnesium, calcium, strontium, barium, radium, scandium, yttrium, titanium, zirconium, hafnium, vanadium, niobium, tantalum, chromium, molybdenum, tungsten, osmium, rhodium, iridium, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

Such other precursors are well known in the pertinent technical field, and the manufacturing methods thereof are also well known. For example, where an alcohol compound is used as the organic ligand, the precursor can be manufactured by conducting a reaction of the abovementioned inorganic metal salt or a hydrate thereof and the alkali metal alkoxide of the alcohol compound. Examples of the inorganic metal salt and hydrate thereof include metal halides and nitrates, and examples of the alkali metal alkoxides include sodium alkoxide, lithium alkoxide, and potassium alkoxide.

In the case of a single source method, it is preferred that the other precursor be a compound demonstrating thermal and/or oxidative decomposition behavior similar to that of the compound of the present invention. In the case of a cocktail source method, it is preferred that the other precursor be a compound demonstrating similar thermal and/or oxidative decomposition behavior and further demonstrating no transformations induced by chemical reactions or the like at the time of mixing.

Compounds represented by Formulas (II-1) to (II-5) below are examples of precursors including titanium, zirconium, or hafnium among the other precursors.

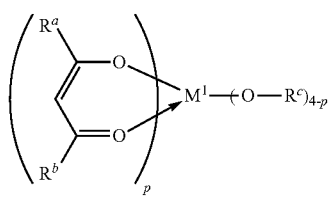

(II-1)

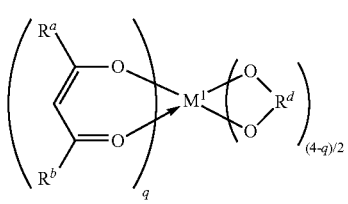

(II-2)

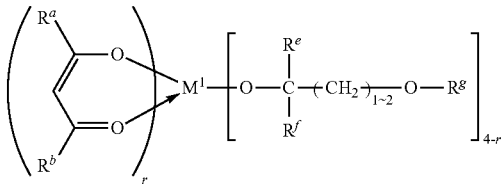

(II-3)

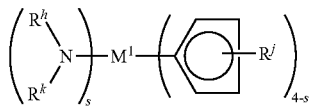

(II-4)

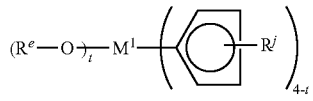

(II-5)

In the formulas, $M^1$ represents titanium, zirconium, or hafnium; $R^a$ and $R^b$ each independently represent an alkyl group having 1 to 20 carbon atoms, which may be substituted with a halogen atom and may contain an oxygen atom in a chain; $R^c$ represents an alkyl group having 1 to 8 carbon atoms; $R^d$ represents an optionally branched alkylene group having 2 to 18 carbon atoms; $R^e$ and $R^f$ each independently represent a hydrogen atom or an alkyl group having 1 to 3 carbon atoms; $R^g$, $R^h$, $R^k$, and $R^j$ each independently represent a hydrogen atom or an alkyl group having 1 to 4 carbon atoms; p represents an integer of 0 to 4; q represents 0 or 2; r represents an integer of 0 to 3; s represents an integer of 0 to 4; and t represents an integer of 1 to 4.

Examples of the alkyl group having 1 to 20 carbon atoms, which may be substituted with a halogen atom and may contain an oxygen atom in a chain, this group being represented by $R^a$ and $R^b$ in Formulas (II-1) to (11-5), include methyl group, ethyl group, propyl group, isopropyl group, butyl group, sec-butyl group, tert-butyl group, isobutyl group, pentyl group, isopentyl group, neopentyl group, tert-pentyl group, hexyl group, cyclohexyl group, 1-methylcyclohexyl group, heptyl group, 3-heptyl group, isoheptyl group, tert-heptyl group, n-octyl group, isooctyl group, tert-octyl group, 2-ethylhexyl group, trifluoromethyl group, perfluorohexyl group, 2-methoxyethyl group, 2-ethoxyethyl group, 2-butoxyethyl group, 2-(2-methoxyethoxy)ethyl group, 1-methoxy-1,1-dimethylmethyl group, 2-methoxy-1, 1-dimethylethyl group, 2-ethoxy-1,1-dimethylethyl group, 2-isopropoxy-1,1-dimethylethyl group, 2-butoxy-1,1-dimethylethyl group, and 2-(2-methoxyethoxy)-1,1-dimethylethyl group. The alkyl group having 1 to 8 carbon atoms, which is represented by $R^c$, includes methyl group, ethyl group, propyl group, isopropyl group, butyl group, sec-butyl group, tert-butyl group, isobutyl group, pentyl group, isopentyl group, neopentyl group, tert-pentyl group, hexyl group, 1-ethylpentyl group, cyclohexyl group, 1-methylcyclohexyl group, heptyl group, isoheptyl group, tert-heptyl group, n-octyl group, isooctyl group, tert-octyl group, and 2-ethylhexyl group. The optionally branched alkylene group having 2 to 18 carbon atoms, which is represented by $R^d$, is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol.

Examples of the alkyl group having 1 to 3 carbon atoms, which is represented by $R^e$ and $R^f$, include methyl group, ethyl group, propyl group, and 2-propyl group. Examples of the alkyl group having 1 to 4 carbon atoms, which is represented by $R^g$, $R^h$, $R^j$, and $R^k$, include methyl group, ethyl group, propyl group, isopropyl group, butyl group, sec-butyl group, tert-butyl group, and isobutyl group.

Specific examples of precursors including titanium include tetrakis(alkoxy)titanium such as tetrakis(ethoxy)titanium, tetrakis(2-propoxy) titanium, tetrakis(butoxy) titanium, tetrakis(sec-butoxy) titanium, tetrakis(isobutoxy) titanium, tetrakis(tert-butoxy) titanium, tetrakis(tert-pentyl) titanium, and tetrakis(1-methoxy-2-methyl-2-propoxy)titanium; tetrakis-β-diketonatotitanium such as tetrakis(pentane-2,4-dionato) titanium, (2,6-dimethylheptane-3,5-dionato) titanium, and tetrakis(2,2,6,6-tetramethylheptane-3,5-dionato)titanium; bis(alkoxy)bis(β-diketonato)titanium such as bis(methoxy)bis(pentane-2,4-dionato)titanium, bis(ethoxy)bis(pentane-2,4-dionato)titanium, bis(tert-butoxy)bis(pentane-2,4-dionato) titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato) titanium, bis(methoxy)bis(2,2,6,6-tetramethylheptane-3,5-dionato) titanium, bis(ethoxy)bis(2,2,6,6-tetramethylheptane-3,5-dionato) titanium, bis(2-propoxy)bis(2,6,6,6-tetramethylheptane-3,5-dionato) titanium, bis(tert-butoxy)bis(2,2,6,6-tetramethylheptane-3,5-dionato) titanium, and bis(tert-amyloxy)bis(2,2,6,6-tetramethylheptane-3,5-dionato) titanium; and glycoxybis(β-diketonato) titanium such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris(dialkylamino)titanium such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; (cyclopentadienyl)tris(alkoxy)titanium such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy) titanium, (isopropylcyclopentadienyl)tris(methoxy)titanium, (butylcyclopentadienyl)tris(methoxy)titanium, (isobutylcyclopentadienyl)tris(methoxy)titanium, (tert-butylcyclopentadienyl)tris(methoxy)titanium, and (pentamethylcyclopentadienyl)tris(methoxy)titanium. Examples of precursors including zirconium or hafnium are compounds presented as examples of titanium-containing precursors in which titanium is substituted with zirconium or hafnium.

Examples of precursors including rare earth elements are compounds represented by Formulas (III-1) to (III-3) below.

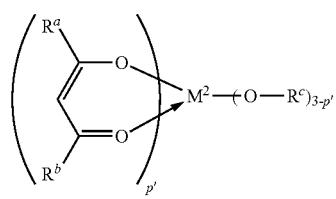
(III-1)

(III-2)

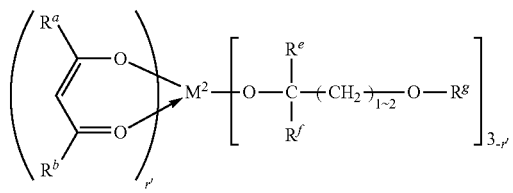
(III-3)

In the formulas, $M^2$ represents a rare earth atom; $R^a$ and $R^b$ each independently represent an alkyl group having 1 to 20 carbon atoms, which may be substituted with a halogen atom and may contain an oxygen atom in a chain; $R^c$ represents an alkyl group having 1 to 8 carbon atoms; $R^e$ and $R^f$ each independently represent a hydrogen atom or an alkyl group having 1 to 3 carbon atoms; $R^g$ and $R^j$ each independently represent an alkyl group having 1 to 4 carbon atoms; p' represents an integer of 0 to 3; and r' represents an integer of 0 to 2.

Examples of rare earth atoms represented by $M^2$ in the precursor including a rare earth element include scandium, yttrium, lanthanum, cerium, praseodymium, neodymium, promethium, samarium, europium, gadolinium, terbium, dysprosium, holmium, erbium, thulium, ytterbium, and lutetium. Examples of groups represented by $R^a$, $R^b$, $R^c$, $R^e$, $R^f$, $R^g$, and $R^j$ include groups presented by way of examples with respect to the titanium-containing precursors.

If necessary, the raw material for forming a thin film of the present invention may include a nucleophilic reagent to stabilize the compound of the present invention and the other precursor. Examples of the nucleophilic reagent include ethylene glycol ethers such as glyme, diglyme, triglyme, and tetraglyme; crown ethers such as 18-crown-6, dicyclohexyl-18-crown-6,24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; 3-keto esters such as methyl acetoacetate, ethyl acetoacetate, and 2-methoxyethyl acetoacetate; and 3-diketones such as acetylacetone, 2,4-hexanedione, 2,4-heptanedione, 3,5-heptanedione, and dipivaroylmethane. These nucleophilic reagents are used in an amount preferably within a range of 0.1 mol to 10 mol, more preferably 1 mol to 4 mol per mole of the amount of the entire precursor.

In the raw material for forming a thin film of the present invention, the amount of metal element impurities, halogen impurities such as chlorine-containing impurities, and organic impurities, which are different from the components constituting the raw materials, needs to be minimized. The content of the metal element impurities is preferably 100 ppb or less, and more preferably 10 ppb or less for each element, and the total amount of the impurities is preferably 1 ppm or less, and more preferably 100 ppb or less. In particular, when the raw material is used to form a gate insulating layer, a gate film, or a barrier layer of an LSI, it is necessary to reduce the amount of alkali metal elements and alkaline earth metal elements which affect the electric properties of a thin film to be obtained. The amount of the halogen impurities is preferably 100 ppm or less, more preferably 10 ppm or less, and most preferably 1 ppm or less. The total amount of organic impurities is preferably 500 ppm or less, more preferably 50 ppm or less, and most preferably 10 ppm or less. Since moisture causes particle generation in the raw material for chemical vapor deposition or particle generation during thin film formation, it is better to remove moisture as much as possible prior to use from the precursor, the organic solvent, and the nucleophilic reagent in order to reduce the amount of moisture therein. The amount of moisture in each of the precursor, the organic solvent, and the nucleophilic reagent is 10 ppm or less, and more preferably 1 ppm or less.

Further, in order to reduce or prevent the particle contamination of the thin film to be formed, it is preferred that the raw material for forming a thin film of the present invention include as few particles as possible. More specifically, in particle measurements with a particle detector of a light scattering type in a liquid phase, the number of particles larger than 0.3 μm is preferably 100 or less in 1 mL of the liquid phase, more preferably the number of particles larger than 0.2 μm is 1000 or less in 1 mL of the liquid phase, and most preferably the number of particles larger than 0.2 μm is 100 or less in 1 mL of the liquid phase.

A method for manufacturing a thin film of the present invention by which a thin film is manufactured by using the raw material for forming a thin film of the present invention is based on the CVD method in which a vapor produced by vaporizing the raw material for forming a thin film of the present invention, and an optionally used reactive gas are introduced into a film formation chamber in which a substrate is disposed, and the precursor is then decomposed and/or chemically reacted on the substrate to grow and deposit a thin film including a metal on the substrate surface. The method for delivering and feeding the raw materials, the deposition method, manufacturing conditions, and manufacturing apparatus are not particularly restricted, and well-known typical conditions and methods can be used.

Examples of the optionally used reactive gas include oxidative gases such as oxygen, ozone, nitrogen dioxide, nitrogen monoxide, water vapor, hydrogen peroxide, formic acid, acetic acid, and acetic anhydride; reductive gases such as hydrogen; and gases producing nitrides, for example, organic amine compounds such as monoalkylamines, dialkylamines, trialkylamines, and alkylenediamines, hydrazine, and ammonia. These gases can be used individually or in combinations of two or more thereof.

Examples of the delivery and feeding methods include the above-described gas delivery method, liquid delivery method, single source method, and cocktail source method.

Examples of the deposition method include thermal CVD in which a source gas or a source gas and a reactive gas are reacted only by heat in order to deposit a thin film; plasma CVD in which heat and plasma are used; photo-excited CVD in which heat and light are used; photo- and plasma-excited CVD in which heat, light and plasma are used; and ALD in which the CVD deposition reaction is separated into elementary steps and deposition is performed step by step at a molecular level.

Examples of the substrate material include silicon, silicon oxide such as quartz, ceramics such as silicon nitride, titanium nitride, tantalum nitride, titanium oxide, titanium nitride ruthenium oxide, zirconium oxide, hafnium oxide, and lanthanum oxide; glass; and metals such as metallic ruthenium. In particular, when the compound where M in General Formula (1) above is cobalt is used as a raw material for forming a thin film by the ALD method, a cobalt-containing thin film can be selectively formed only on a pattern of a copper layer or ruthenium layer which is previously formed on a silicon substrate or silicon oxide substrate, because there is a unique property that a cobalt-containing thin film cannot be formed on the surface of silicon and silicon oxide. The substrate may be in the form of a sheet, sphere, fibers, and flakes. The substrate surface may be flat or may have a three-dimensional structure such as a trench structure.

The manufacturing conditions include the reaction temperature (substrate temperature), reaction pressure, deposition rate, and the like. The reaction temperature is preferably 100° C. or higher, at which the compound of the present invention is sufficiently reactive, and more preferably 150° C. to 400° C. Since the compound of the present invention can be thermally decomposed at a temperature lower than 250° C., a temperature of 150° C. to 250° C. is especially desirable. The reaction pressure is preferably from atmospheric pressure to 10 Pa for thermal CVD and photo-excited CVD, and preferably from 2000 Pa to 10 Pa when plasma is used.

The deposition rate can be controlled by the raw material feed conditions (vaporization temperature and vaporization pressure), reaction temperature, and reaction pressure. Since a high deposition rate can degrade the properties of the resulting thin film and a low deposition rate can cause problems with productivity, the deposition rate is preferably 0.01 nm/min to 100 nm/min and more preferably 1 nm/min to 50 nm/min. In the ALD method, the control is performed by the number of cycles so as to obtain the desired film thickness.

The temperature or pressure during vaporization of the raw material for forming a thin film can be also considered as the manufacturing condition. The step of obtaining the vapor by vaporizing the raw material for forming a thin film may be performed inside the raw material container or inside the vaporization chamber. In either case, it is preferred that the raw material for forming a thin film of the present invention be evaporated at 0° C. to 150° C. Further, where the raw material for forming a thin film is vaporized to obtain the vapor inside the raw material container or vaporization chamber, it is preferred that the pressure inside the raw material container and the pressure inside the vaporization chamber be 1 Pa to 10000 Pa.

The method for manufacturing a thin film of the present invention, when it is realized by the ALD method, may include a raw material introduction step in which the raw material for forming a thin film is vaporized to obtain a vapor and the vapor is introduced into the film formation chamber by the abovementioned delivery and feeding method, and also a precursor thin film formation step of forming a precursor thin film on the surface of the substrate with the compound in the vapor, an evacuation step of evacuating the unreacted compound gas, and a metal-containing thin film formation step of chemically reacting the precursor thin film with a reactive gas and forming a thin film including the metal on the surface of the substrate.

Each of the abovementioned steps will be described hereinbelow in greater detail. When a thin film including at least one type of atom selected from a copper atom, iron atom, nickel atom, cobalt atom and manganese atom is formed by the ALD method, initially, the raw material introduction step, which has been explained hereinabove, is performed. The temperature and pressure preferred when vaporizing the raw material for forming a thin film are the same as explained hereinabove. Then, a precursor thin film is formed on the substrate surface with the compound introduced in the deposition reaction unit (precursor thin film formation step). At this time, heat may be applied by heating the substrate or heating the deposition reaction unit. The precursor thin film which is formed in this step is a thin film generated from the compound of the present invention or a thin film generated by decomposition and/or reaction of part of the compound of the present invention and has a composition different from the target metal-containing thin film. The substrate temperature employed in this step is preferably from room temperature to 500° C., more preferably from 150° C. to 350° C. The pressure in the system (in the film formation chamber) when this step is performed is preferably 1 Pa to 10000 Pa, more preferably 10 Pa to 1000 Pa.

The unreacted compound gas and byproduct gas are then evacuated from the deposition reaction unit (evacuation step). The unreacted compound gas and byproduct gas are ideally completely evacuated from the deposition reaction unit, but such complete evacuation is not always necessary. Examples of the evacuation method include a method of purging the interior of the system with an inactive gas such as nitrogen, helium, and argon, a method of evacuating by depressurizing the interior of the system, and a method in which the aforementioned methods are combined. The degree of depressurization when the depressurization method is used is preferably 0.01 Pa to 300 Pa, more preferably 0.01 Pa to 100 Pa.

The reactive gas is then introduced into the deposition reaction unit and the target metal-containing thin film is formed from the precursor thin film, which has been formed in the preceding precursor thin film formation step, under the action of the reactive gas or the action of the reactive gas and heat (metal-containing thin film formation step). The temperature when heat is used in this step is preferably from room temperature to 500° C., more preferably from 150° C. to 350° C. The pressure in the system (in the film formation chamber) in which this step is performed is preferably 1 Pa to 10000 Pa, more preferably 10 Pa to 1000 Pa. The compound of the present invention has good reactivity with reactive gases and can yield a high-quality metal-containing thin film with a low residual carbon content.

When the ALD method is used in the above-described manner in the method for manufacturing a thin film of the present invention, thin film deposition performed by a series of operations including the raw material introduction step, precursor thin film formation step, evacuation step, and metal-containing thin film formation step may be taken as one cycle, and such cycles may be repeated a plurality of times till a thin film of a necessary thickness is obtained. In this case, after one cycle is completed, it is preferred that the unreacted compound gas, reactive gas, and byproduct gas be evacuated from the deposition reaction unit in the same manner as in the evacuation step, and the next cycle be thereafter performed.

When a thin film is formed by the ALD method, energy such as plasma, light, and voltage may be applied, and a catalyst may be used. The time period for applying the energy and the time period for using the catalyst are not particularly limited. For example, the energy may be applied and the catalyst may be used when the compound gas is introduced in the raw material introduction step, during heating in the precursor thin film formation step or metal-containing thin film formation step, during evacuation of the interior of the system in the evacuation step, when the reactive gas is introduced in the metal-containing thin film formation step, and also between the aforementioned steps.

Further, in the method for manufacturing a thin film of the present invention, annealing may be performed under an inactive gas atmosphere, an oxidizing atmosphere, or a reducing atmosphere after the thin film deposition to obtain better electric properties, and a reflow step may be employed when bump embedding is needed. In this case, the temperature is 200° C. to 1000° C., preferably 250° C. to 500° C.

Figure 2:
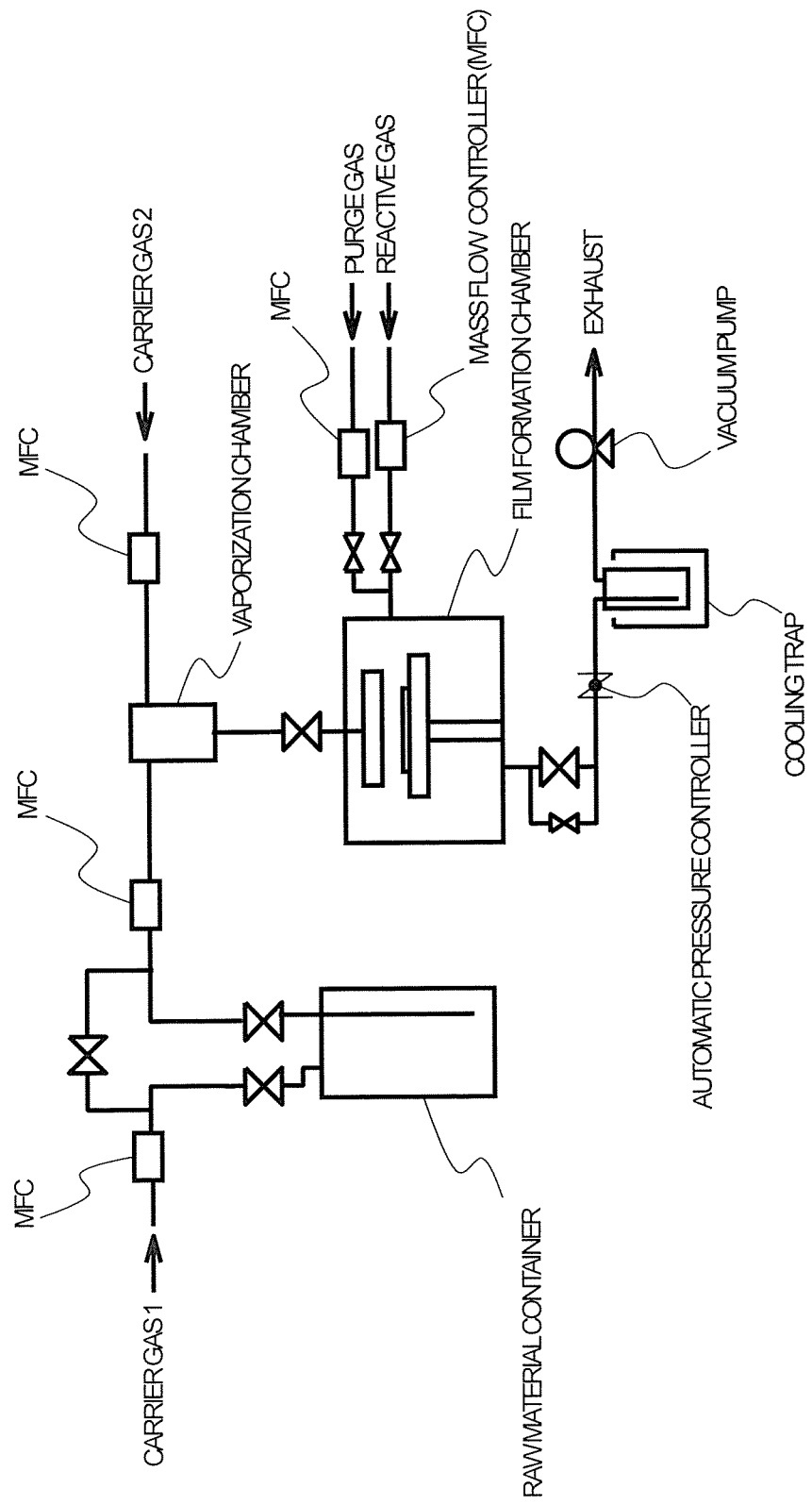
FIG. 2 is a conceptual diagram illustrating another example of a chemical vapor deposition apparatus for use in the method for manufacturing a thin film in the present invention.
Figure 3:
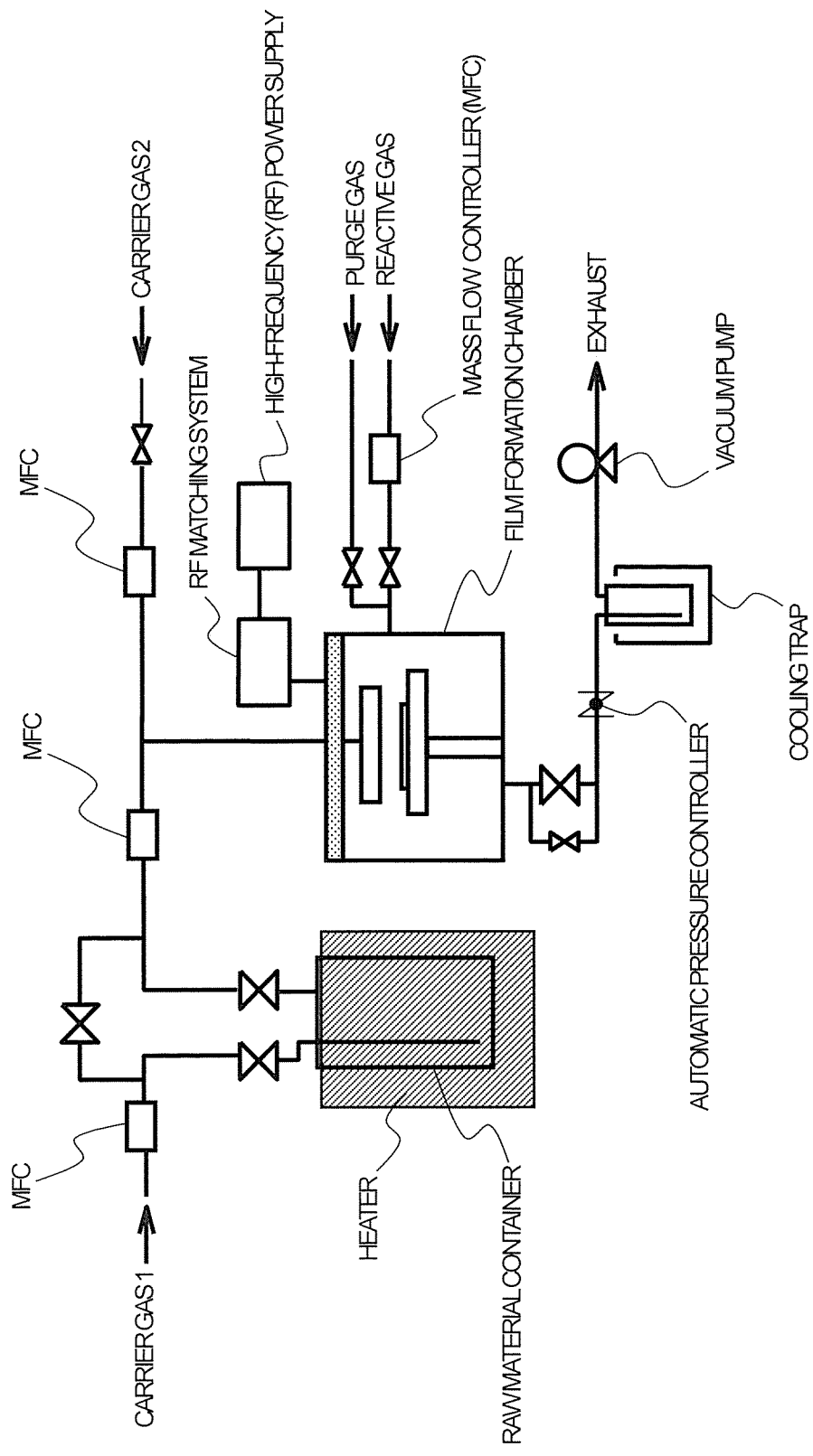
FIG. 3 is a conceptual diagram illustrating another example of a chemical vapor deposition apparatus for use in the method for manufacturing a thin film in the present invention.
Figure 4:
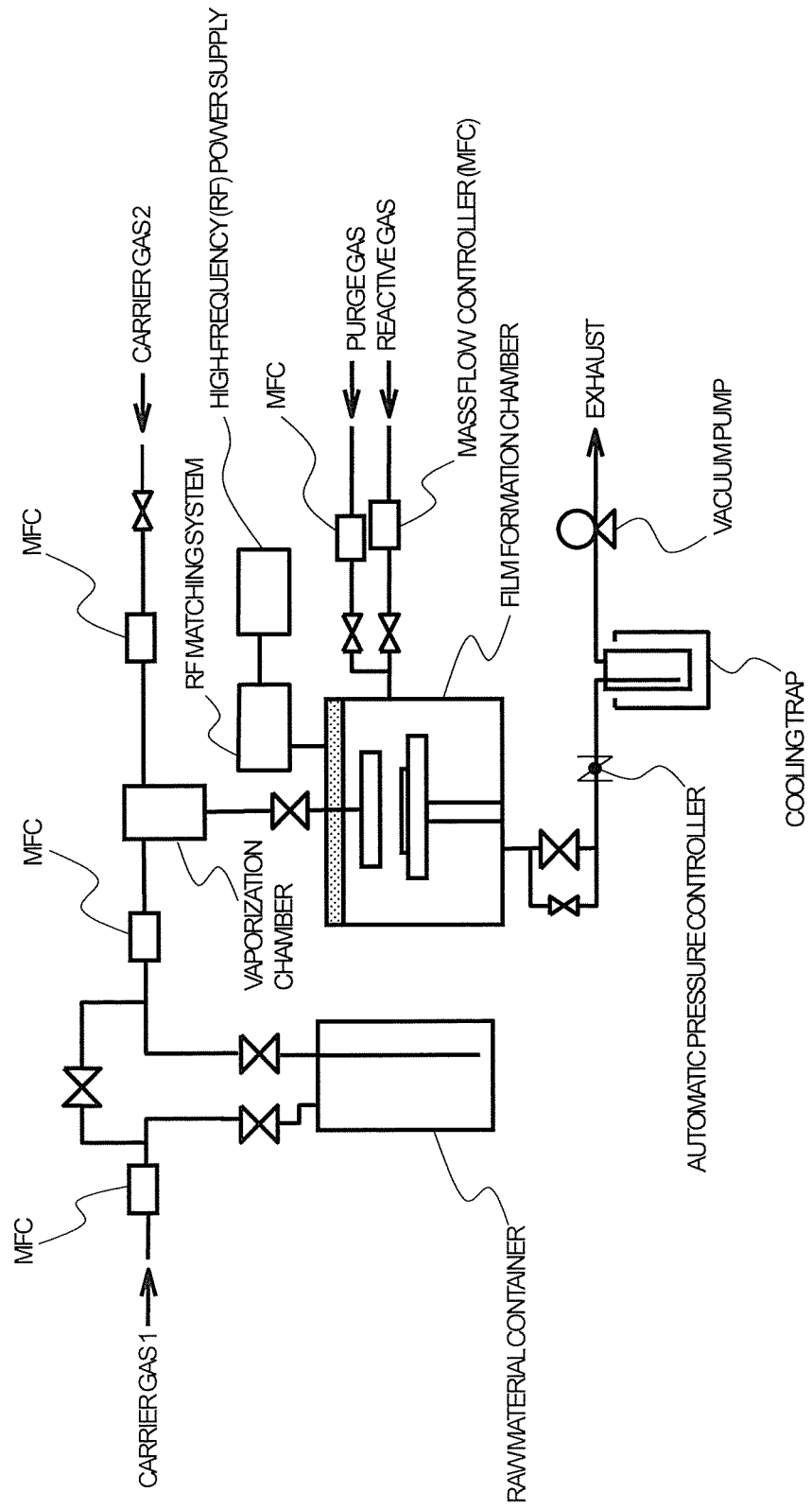
FIG. 4 is a conceptual diagram illustrating another example of a chemical vapor deposition apparatus for use in the method for manufacturing a thin film in the present invention.

A well-known chemical vapor deposition apparatus can be used for manufacturing a thin film by using the raw material for forming a thin film of the present invention. Specific examples of suitable apparatuses include an apparatus, such as depicted in FIG. 1, in which a precursor can be fed by bubbling, and an apparatus, such as depicted in FIG. 2, which has a vaporization chamber. An apparatus can be also used in which, as depicted in FIG. 3 and FIG. 4, plasma treatment can be performed with respect to a reactive gas. The single-substrate apparatuses, such as depicted in FIG. 1 to FIG. 4, are not limiting, and an apparatus which uses a batch furnace and is capable of simultaneous processing of a large number of substrates can be also used.

Where a thin film is manufactured using the raw material for forming a thin film of the present invention, the desired type of thin film such as metal, oxide ceramic, nitride ceramic, and glass can be formed by appropriately selecting the other precursor, reactive gas, and manufacturing conditions. Such thin films are known to exhibit various electric properties, optical properties and the like, and are used for a variety of applications. For example, copper and copper-containing thin films have been used as wiring materials for LSI because of a high electric conductivity, high resistance to electromigration, and a high melting point. Further, nickel and nickel-containing thin films are mainly used for parts of electronic components such as resistive films and barrier films, parts for recording media such as magnetic films, and parts for thin-film solar cells, such as electrodes. Cobalt and cobalt-containing thin films have been used for electrode films, resistive films, adhesive films, magnetic tapes, ultra-hard tool members and the like.

The amidine compound in accordance with the present invention is represent by General Formula (2) below. This compound is especially suitable as a ligand of the precursor used for a thin film manufacturing method having a vaporization step, such as the CVD method.

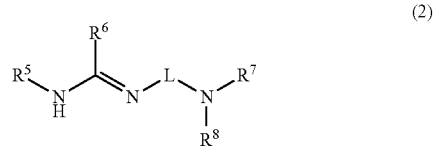

(2)

In the formula, $R^5$ represents a linear or branched alkyl group having 1 to 5 carbon atoms, $R^6$ represents hydrogen or a linear or branched alkyl group having 1 to 5 carbon atoms, $R^7$ and $R^8$ each independently represent a linear or branched alkyl group having 1 to 5 carbon atoms, L represents an alkanediyl group having 1 to 4 carbon atoms. Provided that when $R^5$ represents ethyl group and $R^6$ represents hydrogen, L represents a branched alkanediyl group having 3 carbon atoms or an alkanediyl group having 4 carbon atoms. Provided that when $R^5$ represents ethyl group or tert-butyl group and $R^6$ represents methyl group, L represents an alkanediyl group having 3 or 4 carbon atoms.

Examples of the linear or branched alkyl group having 1 to 5 carbon atoms, which is represented by $R^5$, $R^6$, $R^7$ and $R^8$ in General Formula (2) above, include methyl group, ethyl group, propyl group, isopropyl group, butyl group, isobutyl group, sec-butyl group, tert-butyl group, pentyl group, isopentyl group, and the like.

Examples of the alkanediyl group having 1 to 4 carbon atoms, which is represented by L in General Formula (2) above, include methylene group, ethylene group, propane-1,3-diyl group, propane-1,2-diyl group, butylene group, butane-1,3-diyl group, butane-2,3-diyl group, butane-1,2-diyl group, and the like.

It is preferred that $R^5$ in General Formula (2) above is isopropyl group, isobutyl group, sec-butyl group or tert-butyl group. In particular, the amidine compound where $R^5$ is tert-butyl group is preferred, because the amidine compound has good stability.

The amidine compound where $R^6$ in General Formula (2) above is hydrogen, methyl group or ethyl group is preferred, because the amidine compound produces a metal complex compound having a high vapor pressure when the amidine compound is used as a ligand of the metal complex compound.

The amidine compound where L in General Formula (2) above is ethylene group, propane-1,3-diyl group or propane-1,2-diyl group is preferred, because the amidine compound produces a metal complex compound having a low melting point and a high vapor pressure when the amidine compound is used as a ligand of the metal complex compound. In particular, the amidine compound where L is propane-1,2-diyl group is especially preferred. The amidine compound where $R^7$ and $R^8$ in General Formula (2) above are methyl group or ethyl group is preferred, because the amidine compound produces a metal complex compound having a low melting point and a high vapor pressure when the amidine compound is used as a ligand of the metal complex compound. In particular, the amidine compound where $R^7$ and $R^8$ are methyl group is especially preferred.

Preferred specific examples of the amidine compound represented by General Formula (2) above include Compounds No. 55 to 156 below. In Compounds No. 55 to No. 156, "Me" represents methyl group, "Et" represents ethyl group, "iPr" represents isopropyl group, "sBu" represents sec-butyl group and "tBu" represents tert-butyl group.

Compound No. 55

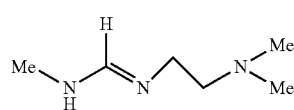

Compound No. 56

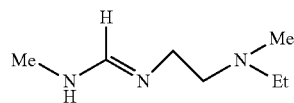

Compound No. 57

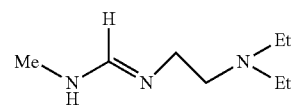

Compound No. 58

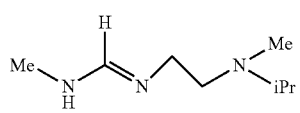

Compound No. 59

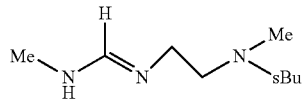

Compound No. 60

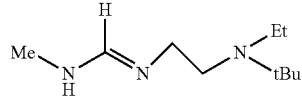

Compound No. 61

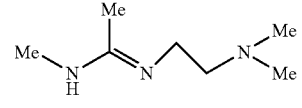

Compound No. 62

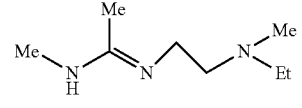

Compound No. 63

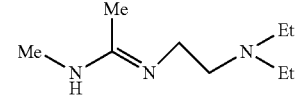

Compound No. 64

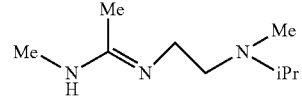

Compound No. 65

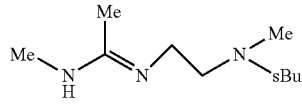

Compound No. 66

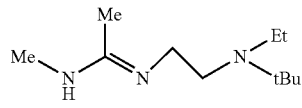

Compound No. 67

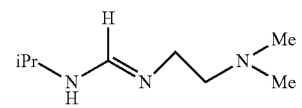

Compound No. 68

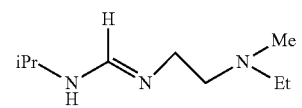

Compound No. 69

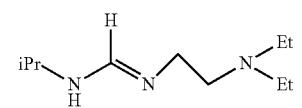

Compound No. 70

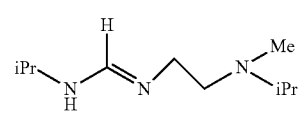

Compound No. 71

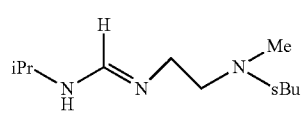

Compound No. 72

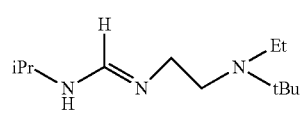

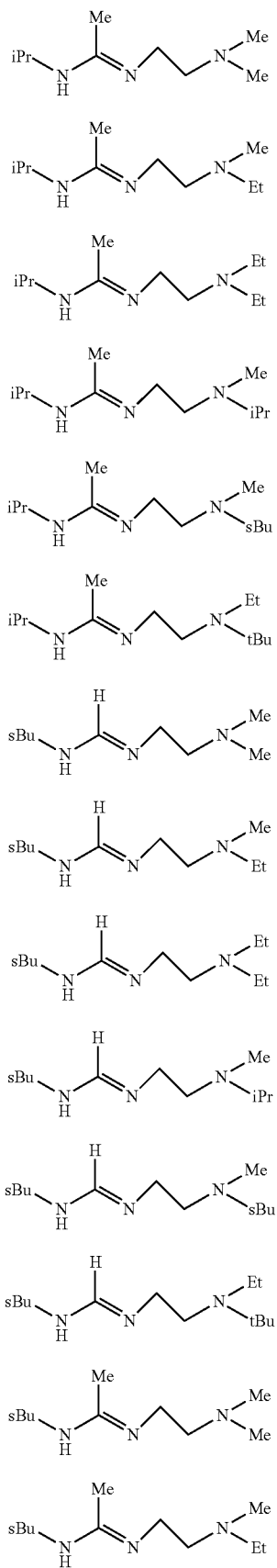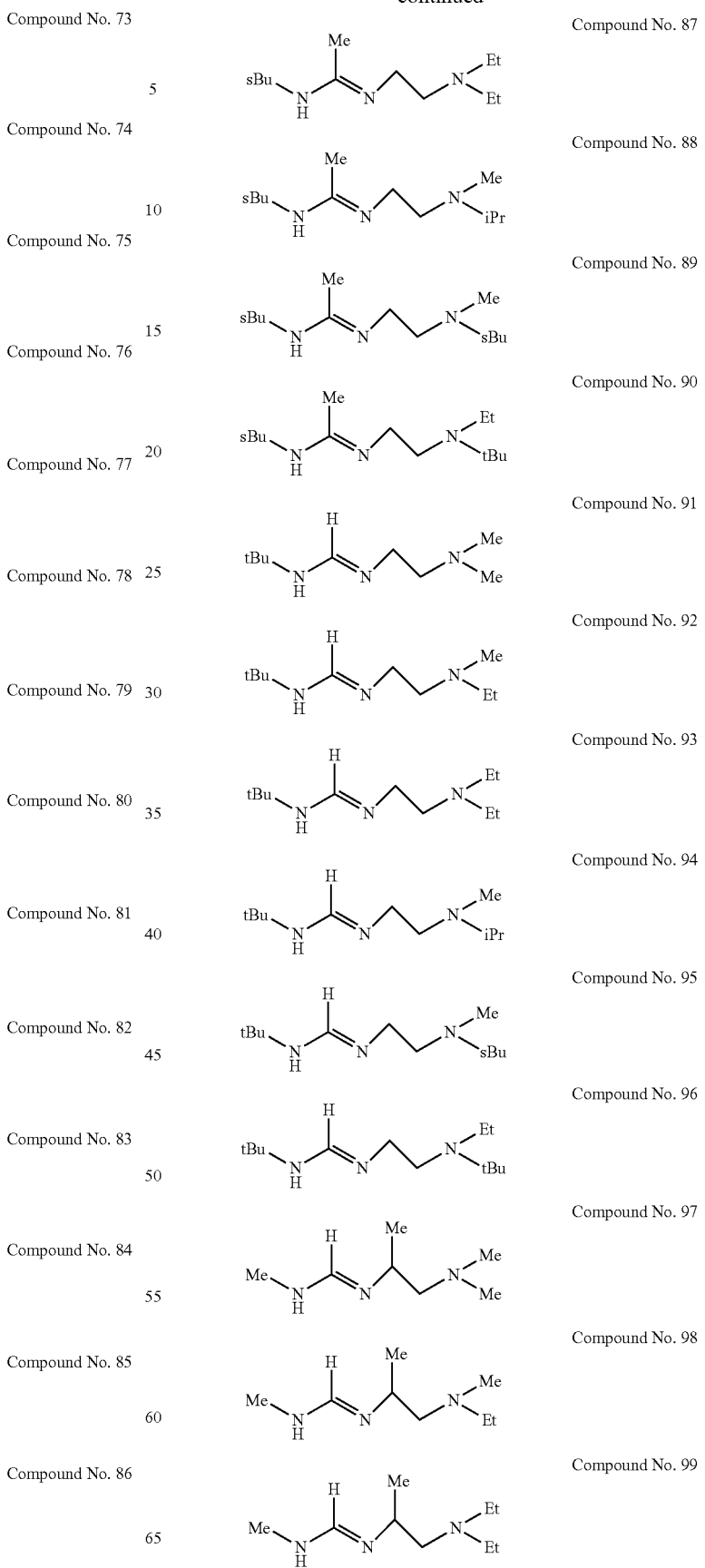

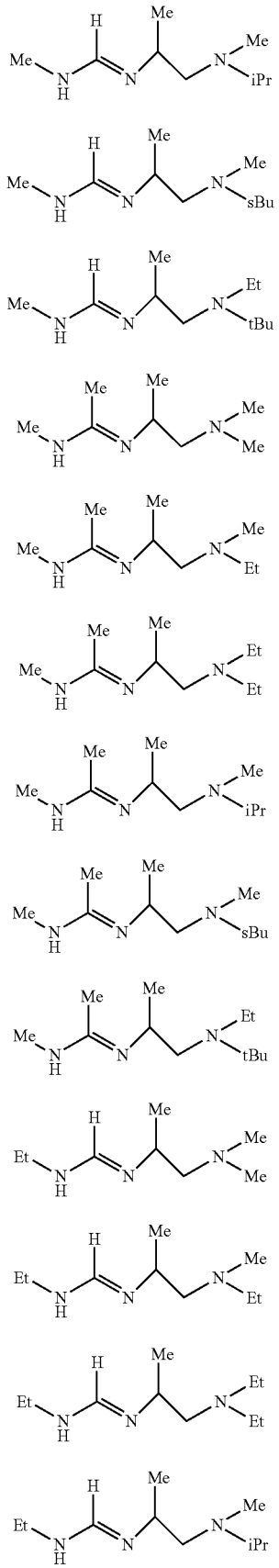
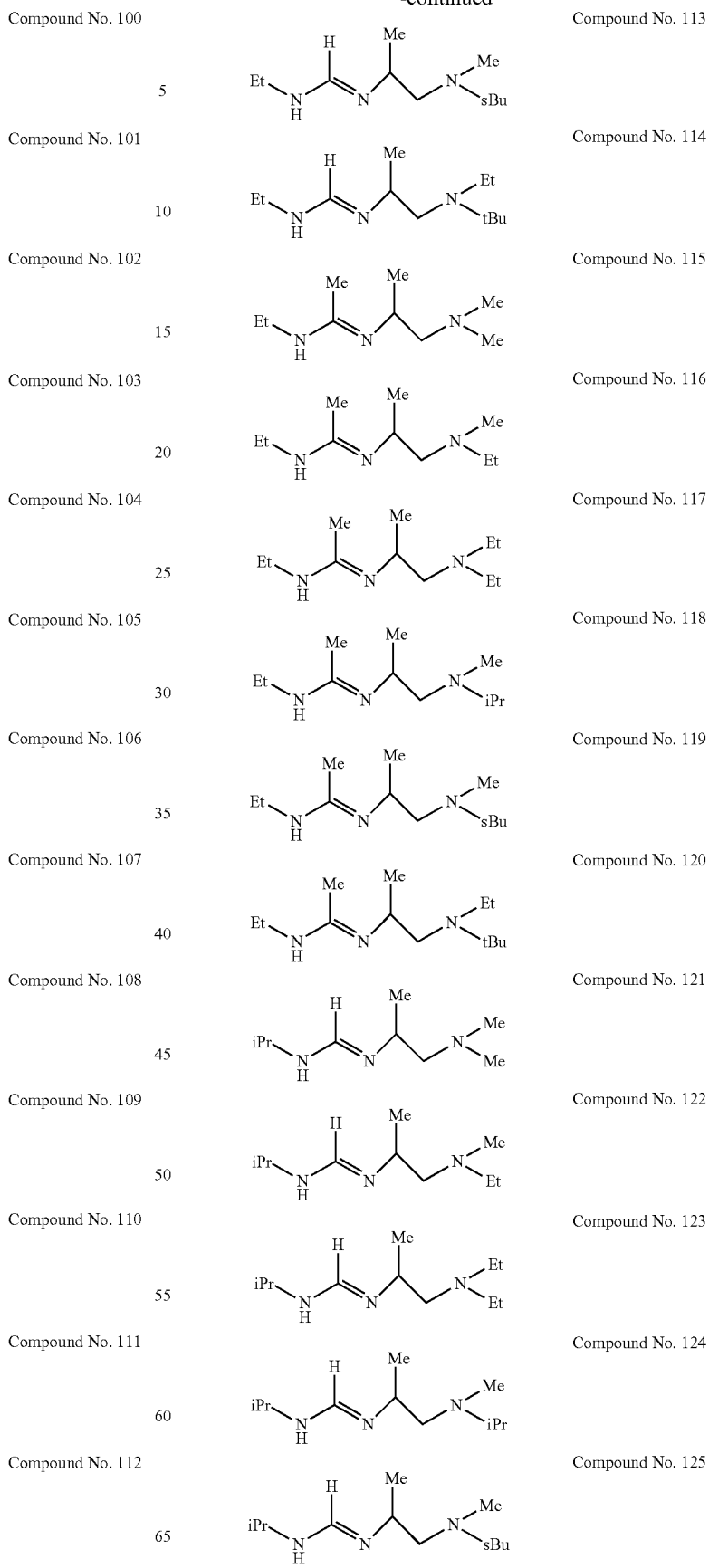
Compound No. 100
Compound No. 101
Compound No. 102
Compound No. 103
Compound No. 104
Compound No. 105
Compound No. 106
Compound No. 107
Compound No. 108
Compound No. 109
Compound No. 110
Compound No. 111
Compound No. 112
Compound No. 113
Compound No. 114
Compound No. 115
Compound No. 116
Compound No. 117
Compound No. 118
Compound No. 119
Compound No. 120
Compound No. 121
Compound No. 122
Compound No. 123
Compound No. 124
Compound No. 125

Compound No. 126: iPr-NH-CH=N-CH(Me)-CH2-N(Et)(tBu)

Compound No. 127: iPr-NH-C(Me)=N-CH(Me)-CH2-N(Me)(Me)

Compound No. 128: iPr-NH-C(Me)=N-CH(Me)-CH2-N(Me)(Et)

Compound No. 129: iPr-NH-C(Me)=N-CH(Me)-CH2-N(Et)(Et)

Compound No. 130: iPr-NH-C(Me)=N-CH(Me)-CH2-N(Me)(iPr)

Compound No. 131: iPr-NH-C(Me)=N-CH(Me)-CH2-N(Me)(sBu)

Compound No. 132: iPr-NH-C(Me)=N-CH(Me)-CH2-N(Et)(tBu)

Compound No. 133: sBu-NH-CH=N-CH(Me)-CH2-N(Me)(Me)

Compound No. 134: sBu-NH-CH=N-CH(Me)-CH2-N(Me)(Et)

Compound No. 135: sBu-NH-CH=N-CH(Me)-CH2-N(Et)(Et)

Compound No. 136: sBu-NH-CH=N-CH(Me)-CH2-N(Me)(iPr)

Compound No. 137: sBu-NH-CH=N-CH(Me)-CH2-N(Me)(sBu)

Compound No. 138: sBu-NH-CH=N-CH(Me)-CH2-N(Et)(tBu)

Compound No. 139: sBu-NH-C(Me)=N-CH(Me)-CH2-N(Me)(Me)

Compound No. 140: sBu-NH-C(Me)=N-CH(Me)-CH2-N(Me)(Et)

Compound No. 141: sBu-NH-C(Me)=N-CH(Me)-CH2-N(Et)(Et)

Compound No. 142: sBu-NH-C(Me)=N-CH(Me)-CH2-N(Me)(iPr)

Compound No. 143: sBu-NH-C(Me)=N-CH(Me)-CH2-N(Me)(sBu)

Compound No. 144: sBu-NH-C(Me)=N-CH(Me)-CH2-N(Et)(tBu)

Compound No. 145: tBu-NH-CH=N-CH(Me)-CH2-N(Me)(Me)

Compound No. 146: tBu-NH-CH=N-CH(Me)-CH2-N(Me)(Et)

Compound No. 147: tBu-NH-CH=N-CH(Me)-CH2-N(Et)(Et)

Compound No. 148: tBu-NH-CH=N-CH(Me)-CH2-N(Me)(iPr)

Compound No. 149: tBu-NH-CH=N-CH(Me)-CH2-N(Me)(sBu)

Compound No. 150: tBu-NH-CH=N-CH(Me)-CH2-N(Et)(tBu)

Compound No. 151: tBu-NH-C(Me)=N-CH(Me)-CH2-N(Me)(Me)

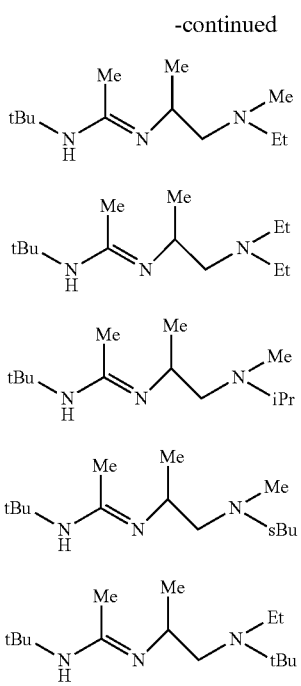

Compound No. 152

Compound No. 153

Compound No. 154

Compound No. 155

Compound No. 156

The amidine compound of the present invention is not limited by the manufacturing method thereof and can be manufactured by using well-known reactions. For example, the amidine compound can be manufactured by the steps of synthesizing a urea having the corresponding structure by using known general methods, synthesizing a carbodiimide compound as an intermediate by reacting the urea with a trialkylamine and p-toluenesulfonyl chloride using dichloromethane and the like as a solvent, reacting the carbodiimide compound with an alkyl lithium dialkyl ether, and purifying the reaction product by distillation and the like.

The amidine compound of the present invention can be used as a ligand of a metal complex compound to be used in a raw material for forming a thin film, and the like. The amidine compound of the present invention can be also used as, for example, a raw material for synthesis of solvents, perfumes, agricultural chemicals, medicines, various polymers and the like.

EXAMPLES

The present invention will be explained hereinbelow in greater detail with reference to Examples and Evaluation Examples. However, the present invention is not limited by the Examples, etc., below.

[Example 1] Manufacture of Compound No. 151

21.3 g (0.215 mol) of tert-butyl isocyanate and 131.7 g of diethyl ether were loaded into a 2 L 4-necked flask and stirred under water cooling. A solution of 22.1 g (0.216 mol) of N,N-dimethylpropane-1,2-diamine and 55.6 g of diethyl ether was added dropwise to this solution. After the end of the dropping, the solution was returned to room temperature and stirred for 3 hours. Thereafter, the solvent was removed at an oil bath temperature of 60° C. under a slightly reduced pressure to obtain 1-(tert-butyl)-3-(1-dimethylaminopropan-2-yl) urea as a colorless oily product. 419.0 g of dichloromethane and 97.8 g (0.966 mol) of triethylamine were loaded into the flask, and stirred under ice cooling. A solution of 83.7 g (0.439 mol) of p-toluenesulfonyl chloride and 641.4 g of dichloromethane was added dropwise to this solution. After the end of the dropping, the solution was returned to room temperature and stirred for 14 hours, and then heated to reflux for 4 hours. After returning the solution to room temperature, the reaction was completed with 40% potassium carbonate aqueous solution. The organic layer was extracted and separated, sodium sulfate was added, and dehydration and filtration were performed. The solvent was removed at an oil bath temperature of 60° C. under a slightly reduced pressure, and after the solvent was distilled off, distillation was performed at an oil bath temperature of 85° C. under a slightly reduced pressure to obtain 26.9 g of colorless transparent carbodiimide compound A in 69% yield. 26.0 g (0.141 mol) of carbodiimide compound A and 51.1 g of diethyl ether were loaded into a 500 mL 4-necked flask and stirred under ice cooling. 130 mL (0.143 mol) of methyl lithium diethyl ether solution was added dropwise to this solution. After the end of the dropping, the solution was returned to room temperature and stirred for 15 hours. Thereafter, water was added dropwise under ice cooling to complete the reaction. The organic layer was extracted and separated, sodium sulfate was added, and dehydration and filtration were performed. The solvent was removed at an oil bath temperature of 70° C. under a slightly reduced pressure, and after the solvent was distilled off, distillation was performed at an oil bath temperature of 85° C. under a slightly reduced pressure to obtain 24.6 g of a colorless transparent target product in 87% yield.

(Analytical Data)
(1) GC-MS m/z: 199 (M+)
(2) $^1$NMR (solvent: heavy benzene) (chemical shift: multiplicity: H number)
(1.28-1.30:d:3) (1.38:s:3) (1.39:s:9) (2.19:s:6) (2.27-2.32:m:1) (3.05:br:1) (3.43:br:1)

[Example 2] Manufacture of Compound No. 2

8.60 g (0.066 mol) of cobalt (II) chloride and 69.5 g of tetrahydrofuran were loaded into a 500 mL 4-necked flask and stirred at room temperature. A solution prepared from 24.4 g (0.132 mol) of Compound No. 151, 85.6 g of normal hexane and 57.6 g (0.132 mol) of nBuLi was added dropwise to the flask under ice cooling. After the end of the dropping, the solution was returned to room temperature and stirred for 17 hours, followed by filtration. The solvent was removed from the obtained filtrate, and the residue was distilled under the conditions of a bath temperature of 160° C., a pressure of 77 Pa and an overhead temperature of 132° C. to obtain the target product as a dark green liquid. The yield amount was 20.0 g and the yield percentage was 66%.

(Analytical Data)
(1) Normal-Pressure TG-DTA
Temperature of 50% mass reduction: 236° C. (Ar flow rate: 100 ml/min, temperature increase rate 10° C./min, sample amount: 9.496 mg)
(2) Elemental Analysis (Metal Analysis: ICP-AES, CHN Analysis: CHN Analyzer)
Cobalt content: 13.0 mass % (theoretical values: 12.94 mass %)
C: 57.9 mass % (theoretical values: 58.00 mass %), H: 10.5 mass % (theoretical values: 10.62 mass %), N: 18.6 mass % (theoretical values: 18.45 mass %)

[Manufacture Example] Manufacture of Well-Known Compound A 10.2 g (0.103 mol) of tert-butyl isocyanate and 73.0 g of diethyl ether were loaded into a 1 L 4-necked flask and stirred under water cooling. A solution of 8.90 g (0.101 mol) of N,N-dimethylethylenediamine and 34.9 g of diethyl ether was added dropwise to this solution. After the end of the dropping, the solution was returned to room temperature and stirred for 3 hours. Thereafter, the solvent was removed at an oil bath temperature of 60° C. under a slightly reduced pressure to obtain 1-(tert-butyl)-3-(2-dimethylaminoethyl) urea as a colorless oily product. 275.3 g of dichloromethane and 45.6 g (0.460 mol) of triethylamine were loaded into the flask, and stirred under ice cooling. A solution of 38.8 g (0.203 mol) of p-toluenesulfonyl chloride and 284.5 g of dichloromethane was added dropwise to this solution. After the end of the dropping, the solution was returned to room temperature and stirred for 2 hours, and the reaction was completed with 40% potassium carbonate aqueous solution. The organic layer was extracted and separated, sodium sulfate was added, and dehydration and filtration were performed. The solvent was removed at an oil bath temperature of 55° C. under a slightly reduced pressure, and after the solvent was distilled off, distillation was performed at an oil bath temperature of 80° C. under a slightly reduced pressure to obtain 9.75 g of colorless transparent carbodiimide compound B in 55.7% yield. 10.5 g (0.062 mol) of carbodiimide compound B and 42.9 g of diethyl ether were loaded into a 200 mL 4-necked flask and stirred under ice cooling. 62 mL (0.062 mol) of methyl lithium diethyl ether solution was added dropwise to this solution. After the end of the dropping, the solution was returned to room temperature and stirred for 16 hours. Thereafter, water was added dropwise under ice cooling to complete the reaction. The organic layer was extracted and separated, sodium sulfate was added, and dehydration and filtration were performed. The solvent was removed at an oil bath temperature of 75° C. under a slightly reduced pressure, and after the solvent was distilled off, distillation was performed at an oil bath temperature of 75° C. under a slightly reduced pressure to obtain 9.67 g of a colorless transparent target product (Well-known compound A shown below) in 84% yield.
(Analytical Data)
(1) GC-MS m/z: 185 (M+)
(2) $^1$NMR (solvent: heavy benzene) (chemical shift: multiplicity: H number)
(1.31:s:3) (1.39:s:9) (2.23:s:6) (2.65:m:2) (3.36-3.40:t:2)

compound A

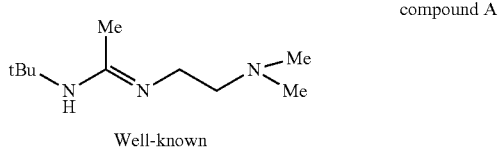 [SMILES: C/C(=N\CCN(C)C)NC(C)(C)C]

Well-known

[Example 3] Manufacture of Compound No. 1

5.31 g (0.041 mol) of cobalt (II) chloride and 74.9 g of tetrahydrofuran were loaded into a 300 mL 3-necked flask and stirred at room temperature. A solution prepared from 15.30 g (0.083 mol) of Well-known compound A, 65.9 g of normal hexane and 35.2 g (0.082 mol) of nBuLi was added dropwise to the flask under ice cooling. After the end of the dropping, the solution was returned to room temperature and stirred for 19 hours, followed by filtration. The solvent was removed from the obtained filtrate, and the residue was purified at a temperature of 130° C. and a pressure of 57 Pa by using a Kugelrohr to obtain a dark green solid.

(Analytical Data)
(1) Normal-Pressure TG-DTA
Temperature of 50% mass reduction: 224° C. (Ar flow rate: 100 ml/min, temperature increase rate 10° C./min, sample amount: 8.619 mg)
(2) Elemental Analysis (Metal Analysis: ICP-AES, CHN Analysis: CHN Analyzer)
Cobalt content: 13.7 mass % (theoretical values: 13.78 mass %)
C: 56.4 mass % (theoretical values: 56.19 mass %), H: 10.3 mass % (theoretical values: 10.37 mass %), N: 19.6 mass % (theoretical values: 19.66 mass %)

[Example 4] Manufacture of Compound No. 157

18.8 g (0.190 mol) of tert-butyl isocyanate and 129.7 g of diethyl ether were loaded into a 2 L 4-necked flask and stirred under water cooling. A solution of 19.4 g (0.190 mol) of N,N-dimethy-1,3-propanediamine and 45.4 g of diethyl ether was added dropwise to this solution. After the end of the dropping, the solution was returned to room temperature and stirred for 3 hours. Thereafter, the solvent was removed at an oil bath temperature of 70° C. under a slightly reduced pressure to obtain 1-(tert-butyl)-3-(3-dimethylaminopropyl) urea as a colorless oily product. 304.2 g of dichloromethane and 83.2 g (0.822 mol) of triethylamine were loaded into the flask, and stirred under ice cooling. A solution of 71.4 g (0.374 mol) of p-toluenesulfonyl chloride and 534.4 g of dichloromethane was added dropwise to this solution. After the end of the dropping, the solution was returned to room temperature and stirred for 14 hours, and the reaction was completed with 40% potassium carbonate aqueous solution. The organic layer was extracted and separated, sodium sulfate was added, and dehydration and filtration were performed. The solvent was removed at an oil bath temperature of 80° C. under a slightly reduced pressure, and after the solvent was distilled off, distillation was performed at an oil bath temperature of 95° C. under a slightly reduced pressure to obtain 6.16 g of colorless transparent carbodiimide compound C in 18% yield. 5.05 g (0.027 mol) of carbodiimide compound C and 41.9 g of diethyl ether were loaded into a 200 mL 4-necked flask and stirred under ice cooling. 25 mL (0.027 mol) of methyl lithium diethyl ether solution was added dropwise to this solution. After the end of the dropping, the solution was returned to room temperature and stirred for 3 hours. Thereafter, water was added dropwise under ice cooling to complete the reaction. The organic layer was extracted and separated, sodium sulfate was added, and dehydration and filtration were performed. The solvent was removed at an oil bath temperature of 80° C. under a slightly reduced pressure, and after the solvent was distilled off, distillation was performed at an oil bath temperature of 100° C. under a slightly reduced pressure to obtain 5.20 g of a colorless transparent target product (Compound No. 157 shown below) in 80% yield.
(Analytical Data)
(1) GC-MS m/z: 199 (M+)
(2) $^1$NMR (solvent: heavy benzene) (chemical shift: multiplicity: H number)
(1.34:s:3) (1.39:s:9) (1.86-1.90:t:2) (2.17:s:6) (2.43-2.47:t:2) (3.23-3.26:t:2)

Compound No. 157

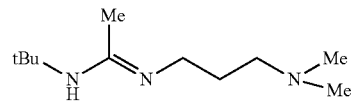

[Example 5] Manufacture of Compound No. 158

1.72 g (0.013 mol) of cobalt (II) chloride and 23.9 g of tetrahydrofuran were loaded into a 100 mL 3-necked flask and stirred at room temperature. A solution prepared from 5.20 g (0.026 mol) of Compound No. 157, 20.9 g of normal hexane and 11.4 g (0.026 mol) of nBuLi was added dropwise to the flask under ice cooling. After the end of the dropping, the solution was returned to room temperature and stirred for 16 hours, followed by filtration. The solvent was removed from the obtained filtrate, and the residue was purified at a temperature of 145° C. and a pressure of 59 Pa by using a Kugelrohr to obtain a dark green liquid (Compound No. 158 shown below). The yield amount was 0.51 g and the yield percentage was 8%.
(Analytical Data)
(1) Normal-Pressure TG-DTA
Temperature of 50% mass reduction: 249° C. (Ar flow rate: 100 ml/min, temperature increase rate 10° C./min, sample amount: 10.121 mg)
(2) Elemental Analysis (Metal Analysis: ICP-AES, CHN Analysis: CHN Analyzer)
Cobalt content: 13.0 mass % (theoretical values: 12.94 mass %)
C: 58.1 mass % (theoretical values: 58.00 mass %), H: 10.5 mass % (theoretical values: 10.62 mass %), N: 18.4 mass % (theoretical values: 18.45 mass %)

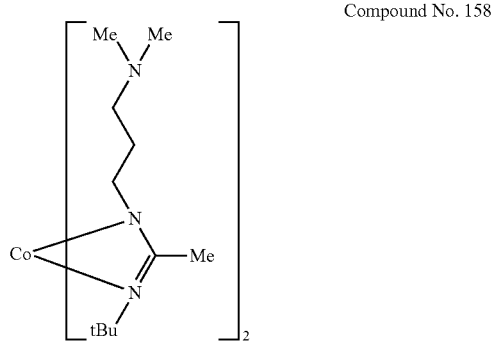

Compound No. 158

[Example 6] Manufacture of Compound No. 159

10.0 g (0.055 mol) of carbodiimide compound A and 78.6 g of diethyl ether were loaded into a 500 mL 4-necked flask and stirred under ice cooling. 230 mL (0.115 mol) of ethyl lithium benzene cyclohexane solution was added dropwise to this solution. After the end of the dropping, the solution was returned to room temperature and stirred for 48 hours, and then heated to reflux for 23 hours. After returning the solution to room temperature, water was added dropwise under ice cooling to complete the reaction. The organic layer was extracted and separated, sodium sulfate was added, and dehydration and filtration were performed. The solvent was removed at an oil bath temperature of 70° C. under a slightly reduced pressure, and after the solvent was distilled off, distillation was performed at an oil bath temperature of 90° C. under a slightly reduced pressure to obtain 8.2 g of a colorless transparent target product (Compound No. 159 shown below) in 66% yield.
(Analytical Data)
(1) GC-MS m/z: 227 (M+)
(2) $^1$NMR (solvent: heavy benzene) (chemical shift: multiplicity: H number) (0.88-0.92:t:3) (1.30-1.32:d:3) (1.41:s:9) (1.75-1.79:m:2) (2.19:s:6) (2.26-2.30:m:1) (3.11:br:1) (3.51:br:1)

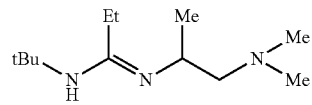

Compound No. 159

[Example 7] Manufacture of Compound No. 8

2.66 g (0.020 mol) of cobalt(II) chloride and 25.0 g of tetrahydrofuran were loaded into a 200 mL 4-necked flask and stirred at room temperature. A solution prepared from 9.20 g (0.040 mol) of Compound No. 159, 23.3 g of normal hexane and 20.2 g (0.047 mol) of nBuLi was added dropwise to the flask under ice cooling. After the end of the dropping, the solution was returned to room temperature and stirred for 16 hours, followed by filtration. The solvent was removed from the obtained filtrate, and the residue was distilled under the conditions of a bath temperature of 170° C., a pressure of 26 Pa and an overhead temperature of 122° C. to obtain a dark green liquid. The yield amount was 4.0 g and the yield percentage was 40%.
(Analytical Data)
(1) Normal-Pressure TG-DTA
Temperature of 50% mass reduction: 244° C. (Ar flow rate: 100 ml/min, temperature increase rate 10° C./min, sample amount: 10.122 mg)
(2) Elemental Analysis (Metal Analysis: ICP-AES, CHN Analysis: CHN Analyzer)
Cobalt content: 12.3 mass % (theoretical values: 12.18 mass %)
C: 59.4 mass % (theoretical values: 59.60 mass %), H: 11.0 mass % (theoretical values: 10.84 mass %), N: 17.3 mass % (theoretical values: 17.38 mass %)

[Example 8] Manufacture of Compound No. 127

24.1 g (0.237 mol) of isopropyl isothiocyanate and 385.8 g of diethyl ether were loaded into a 2 L 4-necked flask and stirred under water cooling. A solution of 26.9 g (0.263 mol) of N,N-dimethypropane-1,2-diamine and 119.8 g of diethyl ether was added dropwise to this solution. After the end of the dropping, the solution was returned to room temperature and stirred for 14 hours. Thereafter, the solvent was removed at an oil bath temperature of 65° C. under a slightly reduced pressure to obtain 1-(1-dimethylaminopropane-2-yl)-3-isopropylthiourea as a colorless oily product. 507.8 g of dichloromethane and 85.0 g (0.840 mol) of triethylamine were loaded into the flask, cooled to −40° C. and stirred. A solution of 46.3 g (0.260 mol) of N-bromosuccinimide and 847.6 g of dichloromethane was added dropwise to this solution. After the end of the dropping, the solution was returned to room temperature and stirred for 16 hours. The reaction was completed with 40% potassium carbonate aqueous solution. The organic layer was extracted and separated, sodium sulfate was added, and dehydration and filtration were performed. The solvent was removed at an oil bath temperature of 80° C. under a slightly reduced pressure, and after the solvent was distilled off, distillation was performed at an oil bath temperature of 90° C. under a slightly reduced pressure to obtain 19.2 g of colorless transparent carbodiimide compound D in 48% yield. 19.2 g (0.113 mol) of carbodiimide compound D and 63.9 g of diethyl ether were loaded into a 500 mL 4-necked flask and stirred under ice cooling. 113 mL (0.113 mol) of methyl lithium diethyl ether solution was added dropwise to this solution. After the end of the dropping, the solution was returned to room temperature and stirred for 15 hours. Thereafter, water was added dropwise under ice cooling to complete the reaction. The organic layer was extracted and separated, sodium sulfate was added, and dehydration and filtration were performed. The solvent was removed at an oil bath temperature of 70° C. under a slightly reduced pressure, and after the solvent was distilled off, distillation was performed at an oil bath temperature of 90° C. under a slightly reduced pressure to obtain 14.3 g of a colorless transparent target product in 69% yield.
(Analytical Data)
(1) GC-MS m/z: 185 (M+)
(2) Elemental analysis (CHN analyzer)
C: 64.5 mass % (theoretical values: 64.81 mass %), H: 12.8 mass % (theoretical values: 12.51 mass %), N: 22.7 mass % (theoretical values: 22.68 mass %)

[Example 9] Manufacture of Compound No. 160

2.34 g (0.018 mol) of cobalt(II) chloride and 22.7 g of tetrahydrofuran were loaded into a 200 mL 4-necked flask and stirred at room temperature. A solution prepared from 6.50 g (0.035 mol) of Compound No. 127, 21.6 g of normal hexane and 15.6 g (0.035 mol) of nBuLi was added dropwise to the flask under ice cooling. After the end of the dropping, the solution was returned to room temperature and stirred for 16 hours, followed by filtration. The solvent was removed from the obtained filtrate, and the residue was distilled under the conditions of a bath temperature of 150° C., a pressure of 40 Pa and an overhead temperature of 115° C. to obtain a dark green liquid (Compound No. 160 shown below). The yield amount was 3.6 g and the yield percentage was 48%.
(Analytical Data)
(1) Normal-Pressure TG-DTA
Temperature of 50% mass reduction: 229° C. (Ar flow rate: 100 ml/min, temperature increase rate 10° C./min, sample amount: 9.637 mg) (2) Elemental analysis (metal analysis: ICP-AES, CHN analysis: CHN analyzer)
Cobalt content: 13.6 mass % (theoretical values: 13.78 mass %)
C: 56.3 mass % (theoretical values: 56.19 mass %), H: 10.2 mass % (theoretical values: 10.37 mass %), N: 19.9 mass % (theoretical values: 19.66 mass %)

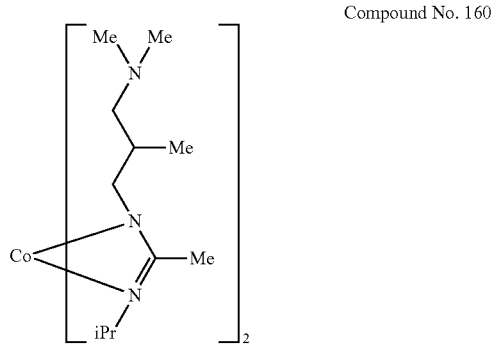

Compound No. 160

[Example 10] Manufacture of Compound No. 139

25.1 g (0.218 mol) of sec-butyl isothiocyanate and 165.9 g of diethyl ether were loaded into a 2 L 4-necked flask and stirred under water cooling. A solution of 24.3 g (0.238 mol) of N,N-dimethypropane-1,2-diamine and 83.6 g of diethyl ether was added dropwise to this solution. After the end of the dropping, the solution was returned to room temperature and stirred for 19 hours. Thereafter, the solvent was removed at an oil bath temperature of 75° C. under a slightly reduced pressure to obtain 1-(sec-butyl)-3-(1-dimethylaminopropane-2-yl)thiourea as a colorless oily product. 409.0 g of dichloromethane and 81.3 g (0.803 mol) of triethylamine were loaded into the flask, cooled to −30° C. and stirred. A solution of 40.9 g (0.230 mol) of N-bromosuccinimide and 695.3 g of dichloromethane was added dropwise to this solution. After the end of the dropping, the solution was returned to room temperature and stirred for 18 hours. The reaction was completed with 40% potassium carbonate aqueous solution. The organic layer was extracted and separated, sodium sulfate was added, and dehydration and filtration were performed. The solvent was removed at an oil bath temperature of 80° C. under a slightly reduced pressure, and after the solvent was distilled off, distillation was performed at an oil bath temperature of 95° C. under a slightly reduced pressure to obtain 9.9 g of colorless transparent carbodiimide compound E in 25% yield. 9.9 g (0.054 mol) of carbodiimide compound E and 37.6 g of diethyl ether were loaded into a 200 mL 4-necked flask and stirred under ice cooling. 54 mL (0.054 mol) of methyl lithium diethyl ether solution was added dropwise to this solution. After the end of the dropping, the solution was returned to room temperature and stirred for 2 hours. Thereafter, water was added dropwise under ice cooling to complete the reaction. The organic layer was extracted and separated, sodium sulfate was added, and dehydration and filtration were performed. The solvent was removed at an oil bath temperature of 70° C. under a slightly reduced pressure, and after the solvent was distilled off, distillation was performed at an oil bath temperature of 85° C. under a slightly reduced pressure to obtain 7.2 g of a colorless transparent target product in 67% yield.
(Analytical Data)
(1) GC-MS m/z: 199 (M+)
(2) Elemental Analysis (CHN Analyzer)
C: 66.5 mass % (theoretical values: 66.28 mass %), H: 12.2 mass % (theoretical values: 12.64 mass %), N: 21.3 mass % (theoretical values: 21.08 mass %)

[Example 11] Manufacture of Compound No. 161

1.71 g (0.013 mol) of cobalt(II) chloride and 15.1 g of tetrahydrofuran were loaded into a 200 mL 4-necked flask and stirred at room temperature. A solution prepared from 5.25 g (0.026 mol) of Compound No. 139, 17.1 g of normal hexane and 11.2 g (0.026 mol) of nBuLi was added dropwise to the flask under ice cooling. After the end of the dropping, the solution was returned to room temperature and stirred for 21 hours, followed by filtration. The solvent was removed from the obtained filtrate, and the residue was distilled under the conditions of a bath temperature of 165° C., a pressure of 40 Pa and an overhead temperature of 127° C. to obtain a dark green liquid (Compound No. 161 shown below). The yield amount was 3.5 g and the yield percentage was 59%.
(Analytical Data)
(1) Normal-Pressure TG-DTA
Temperature of 50% mass reduction: 245° C. (Ar flow rate: 100 ml/min, temperature increase rate 10° C./min, sample amount: 9.605 mg)
(2) Elemental Analysis (Metal Analysis: ICP-AES, CHN Analysis: CHN Analyzer)
Cobalt content: 12.9 mass % (theoretical values: 12.94 mass %)

C: 58.1 mass % (theoretical values: 58.00 mass %), H: 10.5 mass % (theoretical values: 10.62 mass %), N: 18.5 mass % (theoretical values: 18.45 mass %)

Compound No. 161

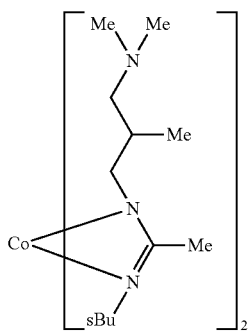

[Evaluation Example 1] Evaluation of Physical Properties of Cobalt Compounds

The states of Compounds No. 2, 1, 158, 8, 160 and 161 and Comparative compound 1 shown below at normal pressure, 30° C. were each visually observed, and the melting point of a solid compound was measured with a micro-melting point measurement apparatus. The temperatures at which the weights of Compound No. 2 and Comparative compound 1 were reduced by 50% under a reduced pressure were measured by TG-DTA. The results are shown in Table 1.
(Reduced Pressure TG-DTA Measurement Conditions)

10 Torr, Ar flow rate: 50 mL/min, temperature increase rate: 10° C./min, sample amount: 9.181 mg (Compound No. 2, Comparative compound 1), 8.587 mg (Compound No. 1), 10.754 mg (Compound No. 158), 9.527 mg (Compound No. 8), 9.919 mg (Compound No. 160), 9.847 mg (Compound No. 161)

Comparative compound 1

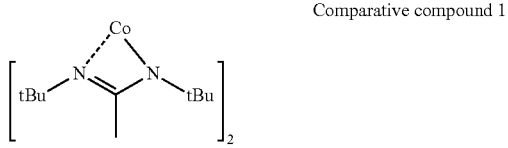

In addition, in Well-known compound A described above, Compounds No. 157 to 161 and Comparative compound 1, "Me" represents methyl group, "Et" represents ethyl group, "iPr" represents isopropyl group, "sBu" represents sec-butyl group and "tBu" represents tert-butyl group.

TABLE 1

| | Compound | State | Melting point [° C.] | Reduced pressure TG-DTA 50% mass reduction temperature [° C.] |
|---|---|---|---|---|
| Evaluation Example 1-1 | Comparative compound 1 | Solid | 105 | 129 |
| Evaluation Example 1-2 | Compound No. 2 | Liquid | — | 155 |
| Evaluation Example 1-3 | Compound No. 1 | Solid | 90 | 159 |
| Evaluation Example 1-4 | Compound No. 158 | Liquid | — | 173 |
| Evaluation Example 1-5 | Compound No. 8 | Liquid | — | 161 |
| Evaluation Example 1-6 | Compound No. 160 | Liquid | — | 155 |
| Evaluation Example 1-7 | Compound No. 161 | Liquid | — | 167 |

It can be seen from Table 1 above that while Comparative compound 1 is a compound with a melting point of 105° C., Compounds No. 2, 8, 158, 160 and 161 are compounds that are liquid under conditions of normal pressure, 30° C. Since a raw material for forming a thin film having a low melting point is easy to transport, such a raw material for forming a thin film can improve productivity. Further, the reduced pressure TG-DTA results show that Compounds No. 1, 2, 8, 158, 160 and 161 have sufficient vapor pressures as a raw material for chemical vapor deposition although these compounds have slightly higher 50% mass reduction temperatures than Comparative compound 1.

[Example 12] Manufacture of Metal Cobalt Thin Film by ALD Method

A metal cobalt thin film was manufactured on a ruthenium (Ru) substrate by ALD method under the following conditions using Compound No. 2 as a raw material for chemical vapor deposition, and using the chemical vapor deposition apparatus shown in FIG. 1. When the film thickness of the resulting thin film was measured by the X-ray reflectivity method and the thin film structure and composition were confirmed by X-ray diffraction method and X-ray photoelectron spectroscopy method, the film thickness was 1 to 3 nm, the film was composed of metal cobalt (confirmed from Co2p peak in XPS analysis), and the residual carbon content in the thin film was below the detection limit of 0.1 atom %. The film thickness obtained per cycle was 0.01 to 0.03 nm.
(Conditions)

Reaction temperature (substrate temperature): 200° C., reactive gas: hydrogen gas
(Steps)

100 cycles were performed, with each cycle consisting of the series of steps shown in (1) to (4) below:

(1) Raw material for chemical vapor deposition that has been vaporized at a material container heating temperature of 110° C. and a material container internal pressure of 100 Pa is introduced, and deposited for 30 seconds at a system pressure of 100 Pa;

(2) Unreacted raw material and byproduct gas are removed by 15 seconds of argon purging;

(3) Reactive gas is introduced, and reacted for 30 seconds at a system pressure of 100 Pa;

(4) Unreacted raw material and byproduct gas are removed by 15 seconds of argon purging.

[Example 13] Manufacture of Metal Cobalt Thin Film by ALD Method

A metal cobalt thin film was manufactured in a manner similar to Example 12, except that Compound No. 1 was used as a raw material for chemical vapor deposition. When the film thickness of the resulting thin film was measured by the X-ray reflectivity method and the thin film structure and composition were confirmed by X-ray diffraction method and X-ray photoelectron spectroscopy method, the film thickness was 0.5 to 1.5 nm, the film was composed of metal cobalt (confirmed from Co2p peak in XPS analysis), and the residual carbon content in the thin film was 0.5 atom %. The film thickness obtained per cycle was 0.005 to 0.015 nm.

A metal cobalt thin film was manufactured in a manner similar to Example 12, except that Compounds No. 8, 158, 160 and 161 were each used as a raw material for chemical vapor deposition. When the film thicknesses of the resulting thin films were measured by the X-ray reflectivity method and the thin film structures and compositions were confirmed by X-ray diffraction method and X-ray photoelectron spectroscopy method, the film thicknesses were 1 to 2 nm, the films were composed of metal cobalt (confirmed from Co2p peak in XPS analysis), and the residual carbon contents in the thin films were 0.2 atom %. The film thicknesses obtained per cycle were 0.01 to 0.02 nm.

Comparative Example 1

A metal cobalt thin film was manufactured on a Ru substrate by ALD method under the following conditions using Comparative compound 1 as a raw material for chemical vapor deposition, and using the chemical vapor deposition apparatus shown in FIG. 1. When the film thickness of the resulting thin film on the Ru substrate was measured by the X-ray reflectivity method and the thin film structure and composition were confirmed by X-ray diffraction method and X-ray photoelectron spectroscopy method, the film thickness was 1 to 2 nm, the film was composed of metal cobalt (confirmed from Co2p peak in XPS analysis), and the residual carbon content in the thin film was 5 atom % or more. The film thickness obtained per cycle was 0.01 to 0.02 nm.

(Conditions)
Reaction temperature (substrate temperature): 200° C., reactive gas: hydrogen gas
(Steps)
100 cycles were performed, with each cycle consisting of the series of steps shown in (1) to (4) below:
(1) Raw material for chemical vapor deposition that has been vaporized at a material container heating temperature of 80° C. and a material container internal pressure of 100 Pa is introduced, and deposited for 30 seconds at a system pressure of 100 Pa;
(2) Unreacted raw material and byproduct gas are removed by 15 seconds of argon purging;
(3) Reactive gas is introduced, and reacted for 30 seconds at a system pressure of 100 Pa;
(4) Unreacted raw material and byproduct gas are removed by 15 seconds of argon purging.

It was found from the results above that good quality metal cobalt thin films could be manufactured by using Compounds No. 1, 2, 8, 158, 160 and 161 as a raw material for forming a thin film by the ALD method. Particularly, Compound No. 2 could manufacture a very good quality metal cobalt thin film. On the other hand, in the case of using Comparative compound 1 as a raw material for forming a thin film by the ALD method, it was possible to obtain a metal cobalt thin film having a high residual carbon content in the thin film, so it was found that there was a difficulty in manufacturing a good quality metal cobalt.

[Example 14] Manufacture of Metal Cobalt Thin Film by ALD Method

An attempt was made to form a metal cobalt thin film on a substrate in which a ruthenium (Ru) layer was formed on half the area of the surface of a $SiO_2$ substrate by ALD method under the following conditions using Compound No. 2 as a raw material for chemical vapor deposition, and using the chemical vapor deposition apparatus shown in FIG. 1. As a result, the thin film was formed only on the Ru layer. When the film thickness of the resulting thin film on the Ru layer was measured by the X-ray reflectivity method and the thin film structure and composition were confirmed by X-ray diffraction method and X-ray photoelectron spectroscopy method, the film thickness was 1 to 3 nm, the film was composed of metal cobalt (confirmed from Co2p peak in XPS analysis), and the residual carbon content in the thin film was below the detection limit of 0.1 atom %. The film thickness obtained per cycle was 0.01 to 0.03 nm. On the other hand, a metal cobalt was not detected on the exposed area of $SiO_2$ of the substrate.

(Conditions)
Reaction temperature (substrate temperature): 150° C., reactive gas: hydrogen gas
(Steps)
100 cycles were performed, with each cycle consisting of the series of steps shown in (1) to (4) below:
(1) Raw material for chemical vapor deposition that has been vaporized at a material container heating temperature of 110° C. and a material container internal pressure of 100 Pa is introduced, and deposited for 30 seconds at a system pressure of 100 Pa;
(2) Unreacted raw material and byproduct gas are removed by 15 seconds of argon purging;
(3) Reactive gas is introduced, and reacted for 30 seconds at a system pressure of 100 Pa;
(4) Unreacted raw material and byproduct gas are removed by 15 seconds of argon purging.

[Example 15] Manufacture of Metal Cobalt Thin Film by ALD Method

A metal cobalt thin film was manufactured in a manner similar to Example 14, except that Compound No. 1 was used as a raw material for chemical vapor deposition. As a result, the thin film was formed only on the Ru layer. When the film thickness of the resulting thin film on the Ru layer was measured by the X-ray reflectivity method and the thin film structure and composition were confirmed by X-ray diffraction method and X-ray photoelectron spectroscopy method, the film thickness was 0.5 to 1.5 nm, the film was composed of metal cobalt (confirmed from Co2p peak in XPS analysis), and the residual carbon content in the thin film was 0.5 atom %. The film thickness obtained per cycle was 0.005 to 0.015 nm.

A metal cobalt thin film was manufactured in a manner similar to Example 14, except that Compounds No. 8, 158, 160 and 161 were each used as a raw material for chemical vapor deposition. As a result, the thin films were formed only on the Ru layer. When the film thicknesses of the resulting thin films on the Ru layer were measured by the X-ray reflectivity method and the thin film structures and compositions were confirmed by X-ray diffraction method and X-ray photoelectron spectroscopy method, the film thicknesses were 1 to 2 nm, the films were composed of metal cobalt (confirmed from Co2p peak in XPS analysis), and the residual carbon contents in the thin films were 0.2 atom %. The film thicknesses obtained per cycle were 0.01 to 0.02 nm.

It was found from the results of Examples 14 and 15 that metal cobalt thin films could be selectively formed depending on the type of substrate by using Compounds No. 1, 2, 8, 158, 160 and 161 as a raw material for forming a thin film by the ALD method. Particularly, Compound No. 2 could manufacture a very good quality metal cobalt thin film.

The present international application claims priority from Japanese Patent Application No. 2016-217749 filed on Nov. 8, 2016, the full contents whereof are incorporated herein by reference.

The invention claimed is:

1. A compound represented by Formula (1) below:

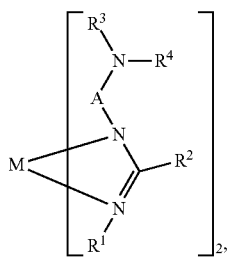

(1)

wherein $R^1$ represents a tert-butyl group, $R^2$ represents a methyl group, $R^3$ and $R^4$ each independently represent a linear or branched alkyl group having 1 to 5 carbon atoms, A represents a propane-1,2-diyl group and M represents copper, nickel, cobalt or manganese.

2. A raw material for forming a thin film, comprising the compound according to claim 1.

3. A method for manufacturing a thin film, said method comprising:

introducing a vapor including a compound obtained by vaporizing the raw material for forming a thin film according to claim 2 into a film formation chamber in which a substrate is disposed;

and forming, on a surface of the substrate, a thin film including at least one type of atom selected from a copper atom, nickel atom, cobalt atom and manganese atom by inducing decomposition and/or chemical reaction of the compound.

4. The compound according to claim 1, wherein in Formula (1), M is cobalt.

* * * * *